United States Patent
Sano et al.

(10) Patent No.: US 10,837,922 B2
(45) Date of Patent: Nov. 17, 2020

(54) X-RAY IMAGING APPARATUS

(71) Applicant: Shimadzu Corporation, Kyoto (JP)

(72) Inventors: Satoshi Sano, Kyoto (JP); Taro Shirai, Kyoto (JP); Takahiro Doki, Kyoto (JP); Akira Horiba, Kyoto (JP); Naoki Morimoto, Kyoto (JP); Kenji Kimura, Kyoto (JP); Hiroshi Mizushima, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 205 days.

(21) Appl. No.: 16/116,720

(22) Filed: Aug. 29, 2018

(65) Prior Publication Data

US 2019/0072503 A1 Mar. 7, 2019

(30) Foreign Application Priority Data

Sep. 1, 2017 (JP) ................... 2017-168996
Apr. 16, 2018 (JP) ................... 2018-078666

(51) Int. Cl.
| | |
|---|---|
| *G01N 23/041* | (2018.01) |
| *G01N 23/20* | (2018.01) |
| *A61B 6/00* | (2006.01) |
| *A61B 6/03* | (2006.01) |
| *G01N 23/20008* | (2018.01) |

(Continued)

(52) U.S. Cl.
CPC ....... *G01N 23/20075* (2013.01); *A61B 6/032* (2013.01); *A61B 6/4291* (2013.01); *A61B 6/44* (2013.01); *A61B 6/484* (2013.01); *G01N 23/041* (2018.02); *G01N 23/201* (2013.01); *G01N 23/20008* (2013.01); *G02B 5/1819* (2013.01);

(Continued)

(58) Field of Classification Search
CPC ....... A61B 6/484; A61B 6/4291; A61B 6/508; A61B 6/0407; G01N 23/041; G01N 2223/3306
See application file for complete search history.

(56) References Cited

U.S. PATENT DOCUMENTS 7,889,838 B2* 2/2011 David .................. A61B 6/4233
378/36
9,649,082 B2* 5/2017 Wischmann ............. A61B 6/06
(Continued)

FOREIGN PATENT DOCUMENTS

| JP | 6173457 B2 | 7/2017 |
|---|---|---|
| WO | 2012/128335 A1 | 9/2012 |
| WO | 2014/030115 A1 | 2/2014 |

OTHER PUBLICATIONS

Schaff et al, "Correlation of X-Ray Vector Radiography to Bone Micro-Architecture", Scientific Reports 4, Article No. 3695 (2014), doi: 10.1038/srep 03695, pp. 1-6.

(Continued)

*Primary Examiner* — David P Porta
*Assistant Examiner* — Fani Boosalis
(74) *Attorney, Agent, or Firm* — Muir Patent Law, PLLC

(57) ABSTRACT

The X-ray imaging apparatus is provided with a plurality of gratings including an X-ray source and a first grating, a detector, a grating rotation mechanism for rotating a plurality of gratings respectively, and an image processor for generating at least a dark field image. The image processor is configured to generate a dark field image captured by arranging the grating at a plurality of angles in a plane orthogonal to the optical axis direction.

18 Claims, 17 Drawing Sheets

First Modification of First Embodiment

(51) Int. Cl.
    *G01N 23/201* (2018.01)
    *G02B 5/18* (2006.01)
(52) U.S. Cl.
    CPC ......... *G02B 5/1838* (2013.01); *G02B 5/1842* (2013.01); *G01N 2223/1016* (2013.01)

(56) References Cited

U.S. PATENT DOCUMENTS

| | | | |
|---|---|---|---|
| 9,717,470 | B2 | 8/2017 | Martens et al. |
| 10,420,521 | B2 * | 9/2019 | Roessl ................. G21K 1/06 |
| 2012/0153181 | A1 | 6/2012 | Iwakiri et al. |
| 2012/0243658 | A1 * | 9/2012 | Geller ................. A61B 6/4291 378/16 |
| 2014/0010344 | A1 * | 1/2014 | Nagatsuka ............. A61B 6/06 378/37 |

OTHER PUBLICATIONS

Prade et al, "Nondestructive characterization of fiber orientation in short fiber reinforced polymer composites with X-ray vector radiography", NDT&E International 86 (2017), pp. 65-72.

Florian Schaff et al: "Correlation of X-Ray Vector Radiography to Bone Micro-Architecture", Scientific Reports, vol. 4, No. 1, (pp. 1-6) Jan. 15, 2014 (Jan. 15, 2014), XP055548059, DOI: 10.1038/srep03695.

Y. Sharma et al.: "Design of Acquisition Schemes and Setup Geometry for Anisotropic X-Ray Dark-Field Tomography (AXDT)", Scientific Reports, vol. 7, No. 1, (pp. 1 to 10) Jun. 9, 2017 (Jun. 9, 2017) XP055548374, DOI:10.1038/s41598-017-03329-0.

Extended European Search Report dated Feb. 5, 2019 in the corresponding European patent application No. 18191150.4.

* cited by examiner

First Embodiment
Grating is arranged laterally
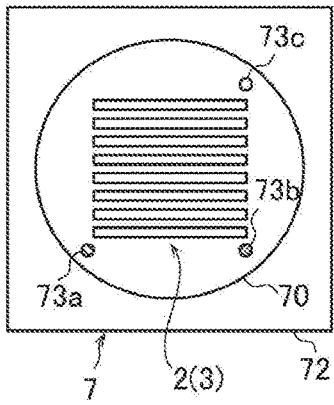
First Embodiment
Grating is arranged obliquely
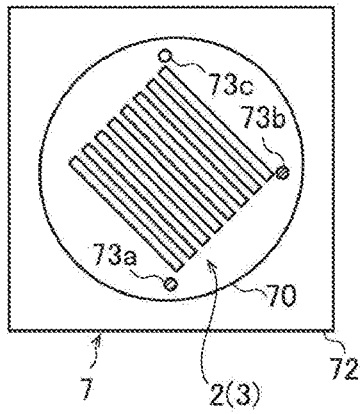
First Embodiment
Grating is arranged vertically
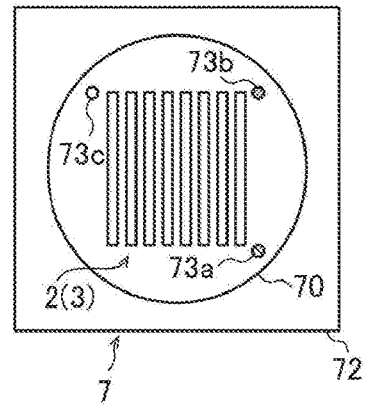
FIG. 3A  FIG. 3B  FIG. 3C
First Embodiment
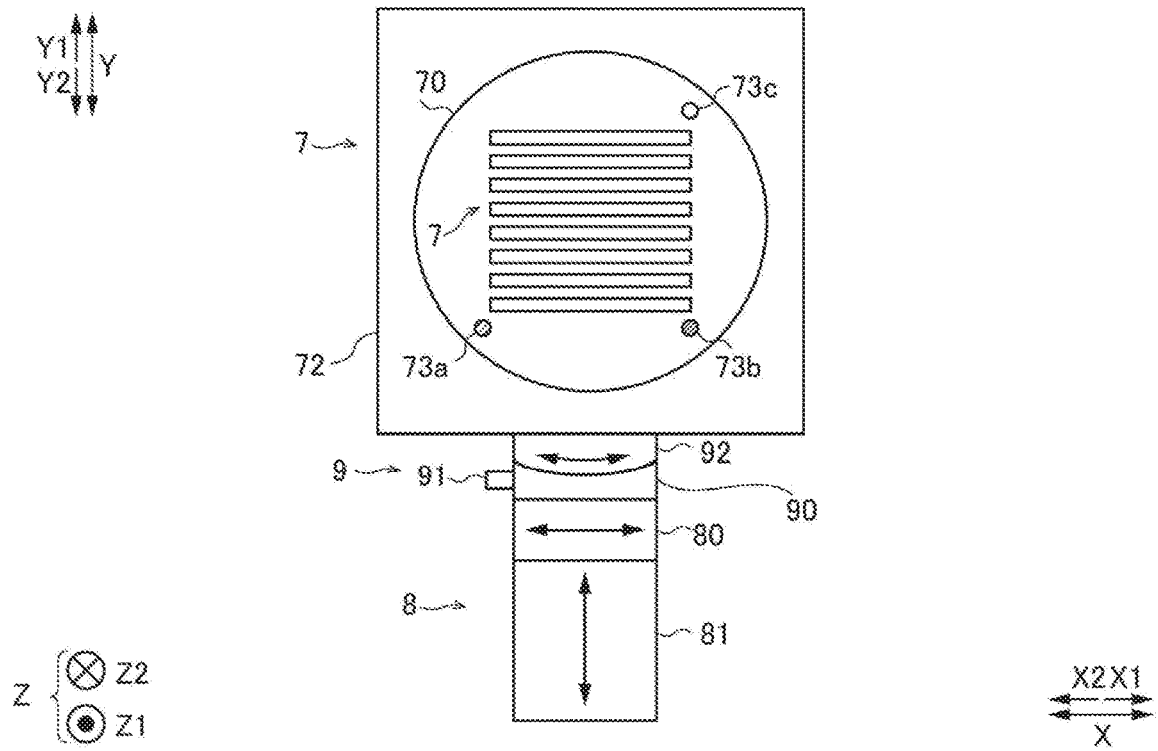
FIG. 4

First Embodiment

First Embodiment

First Embodiment

First Embodiment

First Embodiment

Grating is arranged laterally

13a(13)

First Embodiment

Grating is arranged vertically

13b(13)

Second Embodiment

Second Embodiment

Grating is arranged laterally

Second Embodiment

Grating is arranged vertically

Second Embodiment

Synthesis of lateral direction and vertical direction

Third Embodiment

Third Embodiment
Angle of grating: 0 degree

Third Embodiment
Angle of grating: 45 degrees

Third Embodiment
Angle of grating: 90 degree

Third Embodiment
Angle of grating: 135 degrees

Third Embodiment

— Diffusion in vertical (90°) direction
--- Diffusion in oblique (45°) direction
······ Diffusion in lateral (0°) direction
-·-·- Diffusion in oblique (135°) direction Third Embodiment — Directivity: Strong
--- Directivity: Medium
-·-·- Directivity: Weak Fourth Embodiment Fourth Embodiment First Modification of First Embodiment

X-RAY IMAGING APPARATUS

CROSS-REFERENCE TO RELATED APPLICATIONS

This application claims priority to application number JP2017-168996, entitled "X-ray imaging apparatus", filed on Sep. 1, 2017, invented by Satoshi Sano, Taro Shirai, Takahiro Doki, Akira Horiba, Naoki Morimoto, and Kenji Kimura, and JP2018-078666, entitled "X-ray imaging apparatus", filed on Apr. 16, 2018, invented by Satoshi Sano, Taro Shirai, Takahiro Doki, Akira Horiba, Naoki Morimoto, Kenji Kimura, and Hiroshi Mizushima, the contents of which are hereby incorporated by reference in their entirety.

BACKGROUND OF THE INVENTION

Field of the Invention

The present invention relates to an X-ray imaging apparatus, and more particularly to an X-ray imaging apparatus configured to generate a dark field image.

Description of Background Art

Conventionally, an X-ray imaging apparatus configured to generate a dark field image is known. Such an X-ray imaging apparatus is described in, for example, Florian Schaff, et al., entitled "Correlation of X-Ray Vector Radiography to Bone Micro-Architecture", Scientific Reports 4, Article number; 3695 (2014), doi: 10.1038/srep 03695 (Hereinafter referred to as "Non-Patent Document 1").

In the aforementioned Non-Patent Document 1, an X-ray imaging apparatus configured to generate a dark field image of a subject by a Talbot Lau interferometer is disclosed. The "dark field image" denotes a visibility image obtained by a visibility change based on small-angle scattering of an object. Further, the dark field image is also called small-angle scattering image. The "visibility" denotes sharpness.

Here, when capturing a dark field image, if there is directivity in scattering of X-rays due to an internal structure of a subject, depending on the relationship between the orientation of the grating and the orientation (scattering direction) of the subject with respect to the grating, the internal structure may not be imaged in some cases. Specifically, the X-rays scattering in a direction orthogonal to the orientation of the grating among scattering directions of the X-rays by the internal structure of the subject will be emphasized, so the internal structure can be imaged. However, the X-rays scattering in the direction along the grating direction will be hardly imaged (no sensitivity), and therefore there is a disadvantage that it may be sometimes difficult to image the internal structure in detail depending on the orientation of the subject with respect to the grating. Therefore, in Non-Patent Document 1 described above, the internal structure of the subject is imaged in detail by changing the orientation of the subject with respect to the orientation of the grating. Note that the orientation of the grating denotes a direction along which a grating pattern extends.

However, in Non-Patent Document 1, in order to image the internal structure depending on the orientation of the subject, it is necessary to capture the image by changing the orientation of the subject. Therefore, since imaging is performed by arranging the subject in multiple directions for the purpose of imaging the internal structure of the subject, there is a problem that the orientation of the subject in the images is different. As a result, for example, when comparing the captured X-ray contrast images captured by changing the orientation of the subject with respect to the grating in order to image the internal structure of the subject, there arises a problem that it is necessary to match the orientation of the subject in each image.

The present invention has been made to solve the aforementioned problems, and one object of the present invention is to provide an X-ray imaging apparatus capable of imaging an internal structure of a subject without changing the orientation of the subject with respect to a grating and not requiring matching of the orientation of the subject in each image.

SUMMARY OF THE INVENTION

In order to attain the aforementioned object, an X-ray imaging apparatus according to one aspect of the present invention includes: an X-ray source; a plurality of gratings including a first grating for forming a self-image by X-rays irradiated from the X-ray source and a second grating for causing interference with the self-image of the first grating; a detector configured to detect the X-rays irradiated from the X-ray source; a grating rotation mechanism configured to rotate each of the plurality of gratings in a plane orthogonal to an optical axis direction of the X-rays; and an image processor configured to generate at least a dark field image from an intensity distribution of the X-rays detected by the detector, wherein the image processor is configured to generate the dark field image captured by arranging the gratings at a plurality of angles in the plane orthogonal to the optical axis direction.

In the X-ray imaging apparatus according to one aspect of the present invention, as described above, it includes a grating rotation mechanism configured to rotate each of a plurality of gratings and an image processor configured to generate dark field images captured by arranging the gratings at a plurality of angles. With this, by changing the orientation of the gratings, it is possible to change the orientation of the subject with respect to the gratings without changing the orientation of the subject with respect to the gratings. Therefore, it is possible to image the internal structure of the subject without changing the orientation of the subject with respect to the gratings. Further, since it is possible to image the internal structure of the subject without changing the orientation of the subject with respect to the gratings, for example, even when comparing dark field images captured by arranging the gratings at multiple angles, it is not required to match the orientation of the subject in the images, which enables an easy comparison of images.

In the X-ray imaging apparatus according to the aforementioned one aspect of the present invention, it is preferable that the grating rotation mechanism be configured to arrange the plurality of gratings in at least any two directions among a vertical direction, a lateral direction, and an oblique direction in the plane orthogonal to the optical axis direction.

With this configuration, when the gratings are rotated, it is possible to rotate the plurality of gratings so that the orientations of the gratings with respect to the orientation of the subject are different. As a result, internal structures different in scattering directions of the X-rays within the subject can be imaged, respectively.

In this case, it is preferable to further include a grating moving mechanism configured to move at least one of the plurality of gratings, wherein the grating moving mechanism is configured to move at least one of the plurality of gratings together with the grating rotation mechanism after rotating the plurality of gratings.

With this configuration, even in cases where a grating is moved after rotating the plurality of gratings, it is possible to move the grating without rotating the grating moving mechanism.

In this case, it is preferable that the grating moving mechanism be configured to move the grating in a vertical direction or a lateral direction in the plane orthogonal to the optical axis direction, change a direction in which the grating is moved according to an arrangement direction of the plurality of gratings, and move at least one of the plurality of gratings in a direction in which a distance of a translational movement becomes small when translating any one of the plurality of gratings by at least one grating period or more.

With this configuration, even in cases where the grating is arranged at a plurality of angles and translated, the grating can be translated in a direction in which the distance of the translational movement of the grating decreases according to the arrangement direction of the grating. As a result, it is possible to suppress the image quality degradation due to the errors when the grating is translated.

In a configuration for changing the direction in which the grating is moved depending on the arrangement direction of the plurality of gratings, it is preferably that the grating rotation mechanism include a grating holder configured to hold the grating and a rotating section configured to rotate the grating holder.

With this configuration, for example, comparing with the case in which the gratin is rotated together with the grating moving mechanism, since the grating holder is rotated by the rotating section, the grating rotation mechanism can be miniaturized. Further, since the grating can be rotated by the grating rotation mechanism, it becomes unnecessary to rotate the grating moving unit in conjunction with the rotation of the grating, which can simplify the device configuration.

In this case, it is preferable that the grating rotation mechanism further includes a stopper mechanism configured to switch between a first state in which the grating is rotatable and a second state in which the grating is prevented from being rotated.

By configuring in this manner, by keeping the grating in a non-rotatable state when imaging the subject, it is possible to suppress unintended rotation of the grating, such as, for example, resulting from the malfunction of the grating rotating section. As a result, until imaging is performed after changing the orientation of the grating by the grating rotation mechanism, it is possible to suppress occurrence of an unintended positional displacement in the rotational direction about the optical axis of the grating.

In the configuration in which the grating rotation mechanism includes the stopper mechanism, it is preferable that the stopper mechanism include a contact member that comes into contact with the grating holder, an urging member configured to urge the contact member against the grating holder and a contact state release portion configured to separate the contact member from the grating holder against an urging force of the urging member.

With this configuration, by activating the contact state release portion, it is possible to switch the grating from a non-rotatable state by the urging force of the urging member to a rotatable state. As a result, it becomes possible to make the grating rotatable only when changing the orientation of the grating, so it is possible to minimize the rotational position displacement of the grating with a simple configuration.

In a configuration in which the grating rotation mechanism includes the grating holder and the rotating section, it is preferable that the grating rotation mechanism further include an origin position detector configured to detect an origin position of the grating.

With this configuration, when rotating each grating, it can be easily confirmed whether or not each grating is arranged at the origin position. As a result, when rotating each grating, each grating can be easily arranged at the initial position.

In the configuration in which the grating rotation mechanism includes the grating holder and the rotating section, it is preferable to further include a grating position adjustment mechanism configured to adjust a relative position of at least one of a plurality of gratings among the plurality of gratings, wherein the grating rotation mechanism is configured to be held on the grating moving mechanism via the grating position adjustment mechanism.

With this configuration, even when the grating is rotated by the grating rotation mechanism, the grating position adjustment and the grating movement can be performed without rotating the grating position adjustment mechanism and the grating moving mechanism. As a result, it becomes unnecessary to rotate the grating position adjustment mechanism and the grating moving mechanism in accordance with the rotation of the grating, so it is possible to suppress complication of the device configuration.

In the configuration including the grating position adjustment mechanism, it is preferably to further include a controller configured to calculate an adjustment amount of the grating by the grating position adjustment mechanism based on a moiré fringe that occurs after rotating the plurality of gratings by the grating rotation mechanism.

With this configuration, by rotating the grating, even if there occurs a deviation in the relative position the plurality of gratings among the gratings, it is possible to calculate the adjustment amount of the grating based on the moiré fringe, which enables an easy position adjustment of the grating.

In the X-ray imaging apparatus according to the aforementioned one aspect of the present invention, it is preferable to further include storage configured to store angle information of the plurality of gratings rotated by the grating rotation mechanism.

With such a configuration, at the time of the image analysis, it is possible to easily grasp the direction of the scattered component.

In the X-ray imaging apparatus according to the aforementioned one aspect of the present invention, it is preferable to further include a rotation mechanism configured to relatively rotate an imaging system and a subject, the imaging system including the X-ray source, the detector, and the plurality of gratings, wherein the image processor is configured to generate a three-dimensional dark field image from a plurality of dark field images captured at a plurality of rotation angles while relatively rotating the subject and the imaging system.

Here, the scattering direction of X-rays which is emphasized depending on the direction of the rotation axis and the direction of the grating when performing the relative rotation between the subject and the imaging system. Therefore, there is a case in which it is desired to change the direction of the rotation axis when performing the relative rotation between the subject and the imaging system. In addition, there also is a case in which it is desired to change the orientation of the subject with respect to the rotation axis when performing the relative rotation between the subject and the imaging system.

With this configuration, it is possible to generate a three-dimensional dark field image captured by changing the orientation of the subject with respect to the gratings without changing the direction of the rotation axis when performing the relative rotation between the subject and the imaging system. Further, it is possible to generate a three-dimensional dark field image captured by changing the orientation of the subject with respect to the gratings without changing the orientation of the subject. As a result, it becomes unnecessary to combine the mechanism for changing the direction of the rotation axis and the mechanism for changing the orientation of the subject when performing the relative rotation between the subject and the imaging system, which can suppress complication of the device configuration.

In the X-ray imaging apparatus according to the aforementioned one aspect of the present invention, it is preferable that the image processor is configured to generate a total scattering image representing the intensity of scattering of the X-rays by the subject by synthesizing a plurality of dark field images captured by arranging the gratings at the plurality of angles in the plane orthogonal to the optical axis direction.

Here, since the dark field image is imaged based on the scattering of the X-rays in the subject, the sensitivity varies depending on the orientation of the grating (some scattered images cannot be imaged). By configuring as described above, it is possible to obtain an all-directional scattering image supplementing the sensitivity difference of scattering of the X-rays by the total scattering image generated by synthesizing a plurality of dark field images in which the X-rays are scattered in a plurality of directions. Further, it is possible to image the subject without changing the orientation of the subject, and therefore total scattering images can be generated without performing the position adjustment of the subject. As a result, it is possible to easily and accurately generate the total scattering image.

In this case, it is preferable that the image processor be configured to further generate at least either one of a scattering oriented image representing directivity of scattering of the X-rays by the subject and a directivity intensity image representing strength of directivity of scattering of the X-rays by the subject using the plurality of dark field images different in the angle of the plurality of gratings.

With this configuration, by generating the scattering oriented image, the scattering of the X-rays by the subject can be grasped. Further, by generating the directivity intensity image, the strength of directivity of scattering of the X-rays by the subject can be grasped. As a result, it is possible to grasp the distribution of a plurality of the internal structures in which the directivity of scattering is different within the subject, the distribution of defects occurred in the subject, and the like in more detail.

In the configuration in which the image processor generates a scattering oriented image, it is preferable that the image processor be configured to generate a scattering oriented image in which the directivity of scattering of the X-rays and a color are displayed in an associated manner.

With this configuration, in the scattering oriented image, the directivity of scattering of the X-rays and the color are associated with each other. Therefore, for example, compared with the scattering oriented image in which the difference of directivity is displayed by the pixel value difference (brightness of the image), it is possible to easily grasp the directivity of scattering of the X-rays.

In the X-ray imaging apparatus according to the aforementioned one aspect of the present invention, it is preferable that the image processor be configured to acquire a feature amount of the subject from the image generated by synthesizing the plurality of dark field images.

With such a configuration, it is possible to precisely synthesize the images without performing the positional adjustment, which makes it possible to easily and highly accurately acquire the feature amount.

In the X-ray imaging apparatus according to the aforementioned one aspect of the present invention, it is preferable that the image processor be configured to acquire information on an internal structure having a directivity within the subject as the feature amount of the subject, and the information on the internal structure having a directivity within the subject include at least a length of the internal structure having a directivity and a width of the internal structure having a directivity.

With this structure, it is possible to grasp the shape of the internal structure having a directivity such as the internal structure of the carbon fiber reinforced plastic in more detail.

In the X-ray imaging apparatus according to the one aspect of the present invention, it is preferable that the plurality of gratings further include a third grating arranged between the X-ray source and the first grating.

With this configuration, the coherence of the X-rays irradiated from the X-ray source can be enhanced by the third grating. As a result, it is possible to form the self-image of the first grating without depending on the focal spot size of the X-ray source, so that the freedom of selection of the X-ray source can be improved.

In this case, it is preferably configured such that, in the plurality of gratings, a relative position of any one of the plurality of gratings among the gratings is adjusted, so that the second grating and the third grating are arranged at relative and symmetrical relative positions based on the first grating.

With this configuration, by arranging the position of any one of the first grating, the second grating, and the third grating at relative and symmetrical relative positions based on the first grating, it is possible to perform the position adjustment of the plurality of gratings, and therefore the relative position of the plurality of gratings among the gratings can be easily adjusted.

BRIEF DESCRIPTION OF THE DRAWINGS

FIG. 3A is a schematic diagram in which the orientation of the grating is arranged laterally by the grating rotation mechanism.

FIG. 3B is a schematic diagram in which the orientation of the grating is arranged obliquely by the grating rotation mechanism.

FIG. 3C is a schematic diagram in which the orientation of the grating is arranged vertically by the grating rotation mechanism.

FIG. 4 is a schematic diagram illustrating a grating position adjustment mechanism and a grating moving mechanism in the X-ray imaging apparatus according to the first embodiment.

DESCRIPTION OF PREFERRED EMBODIMENTS

Hereinafter, embodiments of the present invention will be described with reference to the attached drawings.

First Embodiment

With reference to FIG. 1 to FIG. 8, the configuration of an X-ray imaging apparatus 100 according to a first embodiment of the present invention and a method of generating a dark field image 13 by the X-ray imaging apparatus 100 will be described.

(Configuration of X-Ray Imaging Apparatus)

First, with reference to FIG. 1, the configuration of the X-ray imaging apparatus 100 according to the first embodiment will be described.

Figure 1:
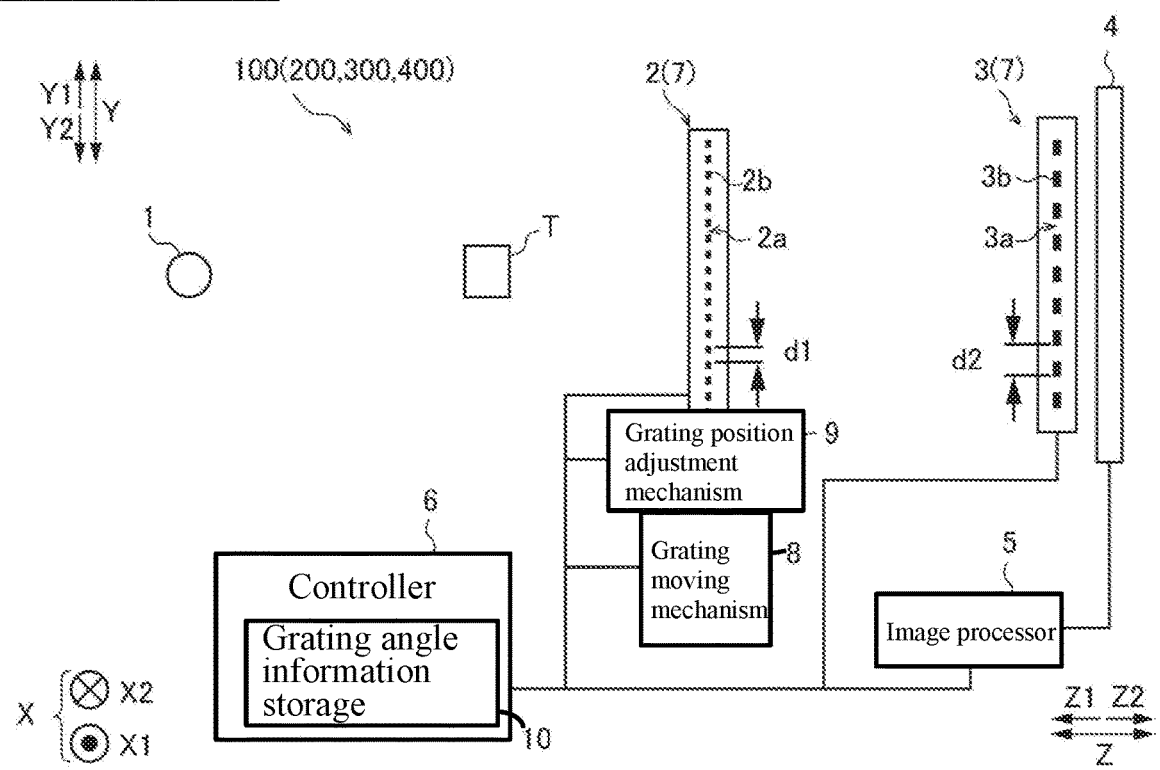
FIG. 1 is a schematic diagram of an X-ray imaging apparatus according to a first embodiment as viewed from an X-direction.

As shown in FIG. 1, the X-ray imaging apparatus 100 is an apparatus for imaging the inside of the subject T by using the scattering of the X-rays that have passed the subject T. Further, the X-ray imaging apparatus 100 is an apparatus for imaging the inside of the subject T using a Talbot effect. For example, in a nondestructive inspection application, the X-ray imaging apparatus 100 can be used for imaging the inside of the subject T as an object.

The subject T includes an internal structure having a directivity. The subject T is, for example, a carbon fiber reinforced plastic (CFRP). Note that an internal structure having a directivity denotes an internal structure characterized by the direction of scattering of X-rays in each of the internal structures. In other words, an internal structure having a directivity denotes an internal structure that scatters X-rays in a predetermined direction.

As shown in FIG. 1, the X-ray imaging apparatus 100 is provided with an X-ray source 1, a first grating 2, a second grating 3, a detector 4, an image processor 5, a controller 6, a grating rotation mechanism 7, a grating moving mechanism 8, and a grating position adjustment mechanism 9.

Note that in the present specification, the direction from the X-ray source 1 to the first grating 2 denotes a Z2-direction, and the direction opposite thereto denotes a Z1-direction. Further note that the left-right direction in the plane orthogonal to the Z-direction denotes an X-direction, the direction toward the back side of the paper surface of FIG. 1 denotes an X2-direction, and the direction toward the front side of the paper surface of FIG. 1 denotes an X1-direction. Further note that the up-and-down direction in the plane orthogonal to the Z-direction denotes a Y-direction, the upward direction thereof denotes a Y1-direction, and the downward direction thereof denotes a Y2-direction. The Z-direction is an example of the "optical axis direction of the X-rays" recited in claims.

The X-ray source 1 is configured to generate X-rays when a high voltage is applied. The X-ray source 1 is configured to irradiate the generated X-rays in the Z2-direction.

The first grating 2 has a plurality of slits 2a and X-ray phase change portions 2b. The slits 2a and the X-ray phase change portions 2b are each arranged at predetermined periods (pitches) d1 in the Y-direction. The slits 2*a* and X-ray phase change portion 2*b* are each formed so as to extend linearly. Further, the slits 2*a* and the X-ray phase change portion 2*b* are each formed so as to extend in parallel. The first grating 2 is a so-called phase grating.

The first grating 2 is arranged between the X-ray source 1 and the second grating 3 and configured to be irradiated by the X-rays from the X-ray source 1. The first grating 2 is provided to form a self-image 12 (see FIG. 6A) of the first grating 2 by the Talbot effect. When X-rays having coherence pass through a grating in which slits are formed, a grating image (self-image 12) is formed at a position away from the grating by a predetermined distance (Talbot distance). This is called a Talbot effect.

The second grating 3 has a plurality of X-ray transmission portions 3*a* and a plurality of X-ray absorption portions 3*b*. The X-ray transmission portions 3*a* and the X-ray absorption portions 3*b* are each arranged at predetermined periods (pitches) d2 in the Y-direction. The X-ray transmission portions 3*a* and the X-ray absorption portions 3*b* are each formed so as to extend linearly. Further, the X-ray transmission portions 3*a* and the X-ray absorption portions 3*b* are each formed so as to extend in parallel with each other. The second grating 3 is a so-called absorption grating. The first grating 2 and the second grating 3 are gratings having different roles, but the slit 2*a* and the X-ray transmission portion 3*a* each transmit X-rays. Also, the X-ray absorption portion 3*b* shields the X-rays. Further, the X-ray phase change portion 2*b* changes the phase of the X-rays according to the difference of the refractive index with respect to the slit 2*a*.

The second grating 3 is arranged between the first grating 2 and the detector 4, and is irradiated by the X-rays that have passed through the first grating 2. Further, the second grating 3 is arranged at a position away from the first grating 2 by the Talbot distance. The second grating 3 interferes with the self-image 12 of the first grating 2 to form a moiré fringe 11 (see FIG. 5) on the detection surface of the detector 4.

The detector 4 is configured to detect the X-rays, convert the detected X-rays into an electric signal, and read the converted electric signal as an image signal. The detector 4 is, for example, an FPD (Flat Panel Detector). The detector 4 is composed of a plurality of conversion elements (not shown) and a plurality of pixel electrodes (not shown) arranged on the plurality of conversion elements. The plurality of conversion elements and the plurality of pixel electrodes are arrayed in the X-direction and the Y-direction at a predetermined periods (pixel pitches). Further, the detector 4 is configured to output the acquired image signal to the image processor 5.

The image processor 5 is configured to generate a dark field image 13 (see FIG. 8A) based on the image signal output from the detector 4. The image processor 5 may be embodied by a single processor or several processors, such as, e.g., a GPU (Graphics Processing Unit) and/or an FPGA (Field-Programmable Gate Array) configured for image processing and/or a conventional microprocessor configured by software for image processing.

The controller 6 is configured to change the orientation of the grating with respect to the subject T by rotating the grating through the grating rotation mechanism 7. In addition, the controller 6 is configured to move the first grating 2 in the vertical direction (Y-direction) or the lateral direction (X-direction) in the grating plane via the grating moving mechanism 8. Also, the controller 6 is configured to change the direction of moving the grating according to the arrangement direction of the grating. The controller 6 includes storage 10 for storing the angle information of the plurality of gratings rotated by the grating rotation mechanism 7. The controller 6 includes, for example, a processor, such as, e.g., a CPU (Central Processing Unit).

The grating rotation mechanism 7 is configured to rotate the first grating 2 and the second grating 3 based on the signal from the controller 6. Specifically, the grating rotation mechanism 7 is provided for each of the first grating 2 and the second grating 3. The grating rotation mechanism 7 is configured to arrange the plurality of gratings in at least two directions among the vertical direction (Y-direction), the lateral direction (X-direction), and the oblique direction in a plane orthogonal to the optical axis direction (Z-direction).

Further, the grating rotation mechanism 7 is configured to change the orientation of the grating with respect to the subject T by rotating the grating. The detailed configuration in which the grating rotation mechanism 7 rotates the grating will be described later.

Note that the vertical direction means that in the case of using the horizontal direction (X-direction) orthogonal to the optical axis direction (Z-direction) of the X-rays as a reference, the direction in which the grating is arranged is approximately 90 degrees. Note that the lateral direction means that in the case of using the horizontal direction (X-direction) orthogonal to the optical axis direction (Z-direction) of the X-rays as a reference, the direction in which the grating is arranged is approximately 0 degrees. Further, the oblique direction means that the direction in which the grating is arranged is approximately plus or minus 45 degrees.

Note that each direction allows a deviation within a range of a predetermined angle. The deviation in the range of the predetermined angle may be, for example, plus or minus 15 degrees or may be plus or minus 5 degrees. Typically, the vertical direction (Y-direction) is a vertical direction and the lateral direction (X-direction) is a horizontal direction.

The grating moving mechanism 8 is configured to move the first grating 2 in the vertical direction (Y-direction) or the lateral direction (X-direction) based on the signal from the controller 6. The detailed configuration that the grating moving mechanism 8 moves the grating will be described later. Further, the grating moving mechanism 8 holds the grating rotation mechanism 7 via the grating position adjustment mechanism 9.

The grating position adjustment mechanism 9 is configured to adjust the relative position of the first grating 2 among the plurality of gratings based on the signal from the controller 6. The detailed configuration for adjusting the relative position of the first grating among the plurality of gratings by the grating position adjustment mechanism 9 will be described later.

Storage 10 is configured to store the grating angle information of the plurality of gratings rotated by the grating rotation mechanism 7 based on the signal from the controller 6. Storage 10 may be composed of any conventional computer storage, for example, an HDD (hard disk drive), SSD (solid state drive), and/or other memory, such as DRAM, NAND, and the like.

In the first embodiment, the image processor 5 is configured to generate a dark field image 13 captured by arranging the grating at a plurality of angles in a plane (XY plane) orthogonal to the optical axis direction (Z-direction). Specifically, the image processor 5 generates dark field images 13 (see FIG. 8A) imaged while translating the first grating 2 through the grating moving mechanism 8 by the controller 6.

Here, the dark field image is an image obtained by imaging the contrast caused by the refraction of the X-rays due to the internal structure in the subject T. Further, in the first embodiment, the image processor 5 is configured to generate a plurality of dark field images 13 captured by arranging the grating at a plurality of angles by rotating the first grating 2 and the second grating 3 via the grating rotation mechanism 7 by the controller 6.

(Grating Rotation Mechanism)

Next, referring to FIG. 2, the configuration of the grating rotation mechanism 7 of the X-ray imaging apparatus 100 according to the first embodiment will be described.

Figure 2:
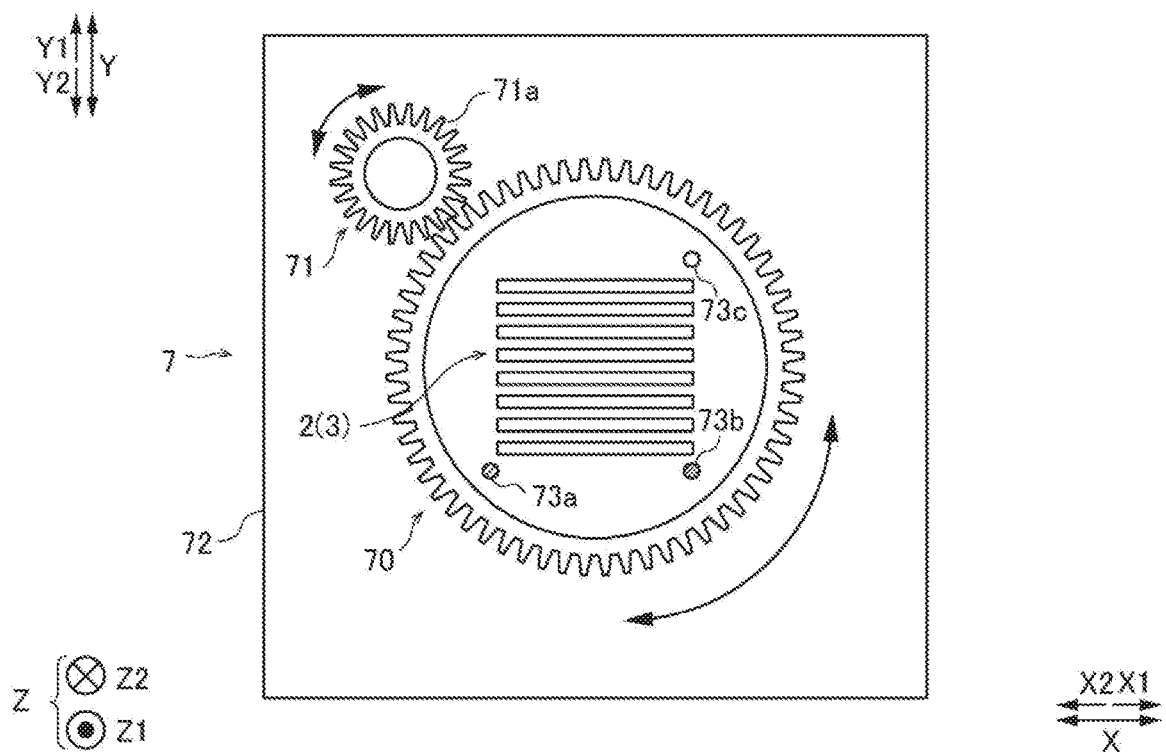
FIG. 2 is a schematic diagram illustrating a grating rotation mechanism in the X-ray imaging apparatus according to the first embodiment.

As shown in FIG. 2, the grating rotation mechanism 7 includes a grating holder 70 for holding the grating, a rotating section 71 for rotating the grating holder 70, and a housing 72. The grating holder 70 is rotatably supported within the housing 72. Further, the grating holder 70 is configured to internally hold the grating in a contact manner.

Further, the grating holder 70 is formed in a disk shape. In the grating holder 70, the outer peripheral surface is formed in a gear shape. It should be noted that in the example shown in FIG. 2, although the grating (grating pattern) is shown in an enlarged manner so that the direction of the grating can be recognized for convenience. In actual, the grating pattern of each grating is very fine and the direction of the grating can be hardly recognized with the naked eye.

Therefore, in the first embodiment, the grating holder 70 is provided with a first marker 73a, a second marker 73b, and a third marker 73c so that the user can confirm the rotation of the grating. As shown in FIG. 2, the first marker 73a, the second marker 73b, and the third marker 73c are configured to be distinguishable from each other. The grating pattern denotes the slit 2a, the X-ray phase change portion 2b, the X-ray transmission portion 3a, the X-ray absorption portion 3b, and the like.

The rotating section 71 includes a power portion (not shown) and a rotation portion 71a. The power portion includes a motor, an encoder, and the like. The rotation portion 71a is formed in a disk shape. Further, the rotation portion 71a has a gear-like outer peripheral surface. Further, the rotation portion 71a is configured to be rotated by the power portion. The grating holder 70 and the rotating section 71 (rotation portion 71a) are formed so as to engage with each other (the gears mesh with each other), and as the rotating section 71 (rotation portion 71a) rotates, the grating holder 70 rotates.

Therefore, the grating rotation mechanism 7 is configured such that the rotating section 71 is rotated based on the signal from the controller 6, and the grating holder 70 is rotated by the rotation of the rotating section 71, thereby rotating the grating.

The movable range of the rotating section 71 may be any range. For example, it may be configured to rotate in the range of approximately 0 degrees to approximately 360 degrees, or it may be configured to rotate in the range of approximately 0 degrees to approximately 180 degrees. Further, it may be configured to rotate in the range from approximately minus 90 degrees to approximately 90 degrees. In the first embodiment, the rotating section 71 is configured to move within the range of approximately 0 degrees to approximately 90 degrees. Further, the rotation angle θ (see FIG. 6B) of the rotating section 71 is stored in storage 10 by an encoder or the like included in the rotating section 71. That is, the angle θ at which each grating is rotated by the grating rotation mechanism 7 is stored in storage 10.

In the first embodiment, the controller 6 can arrange the grating in the orientation as shown in FIG. 3A to FIG. 3C by rotating each grating through the grating rotation mechanism 7. The grating rotation mechanism 7 is configured so that the rotation angle θ of each grating becomes substantially equal. In the first embodiment, the X-ray imaging apparatus 100 is configured to image the subject T in an arrangement in which the grating is oriented vertically (in the Y-direction) and laterally (in the X-direction). Note that the direction of the grating denotes the extending direction of the grating pattern.

(Grating Moving Mechanism and Grating Position Adjustment Mechanism)

As shown in FIG. 4, the grating moving mechanism 8 is configured to move the grating in the vertical direction (Y-direction) or the lateral direction (X-direction) in a plane (XY plane) orthogonal to the optical axis direction (Z-direction).

Specifically, as shown in FIG. 4, the grating moving mechanism 8 includes an X-direction linear motion mechanism 80 and a Y-direction linear motion mechanism 81.

The X-direction linear motion mechanism 80 is configured to translate in the X-direction. The X-direction linear motion mechanism 80 includes, for example, a stepping motor. The Y-direction linear motion mechanism 81 is configured to translate in the Y-direction. The Y-direction linear motion mechanism 81 includes, for example, a stepping motor. The grating moving mechanism 8 is configured to translate the grating rotation mechanism 7 in X-direction via the grating position adjustment mechanism 9 by the operation of the X-direction linear motion mechanism 80. Further, the grating moving mechanism 8 is configured to translate the grating rotation mechanism 7 in Y-direction via the grating position adjustment mechanism 9 by the operation of the Y-direction linear motion mechanism 81. That is, together with the grating rotation mechanism 7, the grating moving mechanism 8 is configured to move the first grating 2.

Further, as shown in FIG. 4, the grating position adjustment mechanism 9 is held on the grating moving mechanism 8. The grating position adjustment mechanism 9 includes a stage support unit 90, a drive unit 91, and a stage 92. The stage support unit 90 supports the stage 92 from below (Y1-direction). The drive unit 91 is configured to reciprocate the stage support unit 90 in the X-direction. The stage 92 is formed in a convexly curved shape toward the stage support unit 90 and configured to be rotated about the center axis in the Z-direction by being reciprocated in the X-direction. Unlike the grating rotation mechanism 7 which changes the orientation of each grating by turning each grating greatly, the grating position adjustment mechanism 9 is a mechanism for adjusting the fine angle deviation of the grating within the XY-plane. Therefore, the grating position adjustment mechanism 9 is configured to have high positional accuracy when compared with the grating rotation mechanism 7. Further, the grating position adjustment mechanism 9 is configured so that the rotation amount of the grating becomes smaller as compared with the grating rotation mechanism 7.

(Position Adjustment of Grating)

Figure 5:
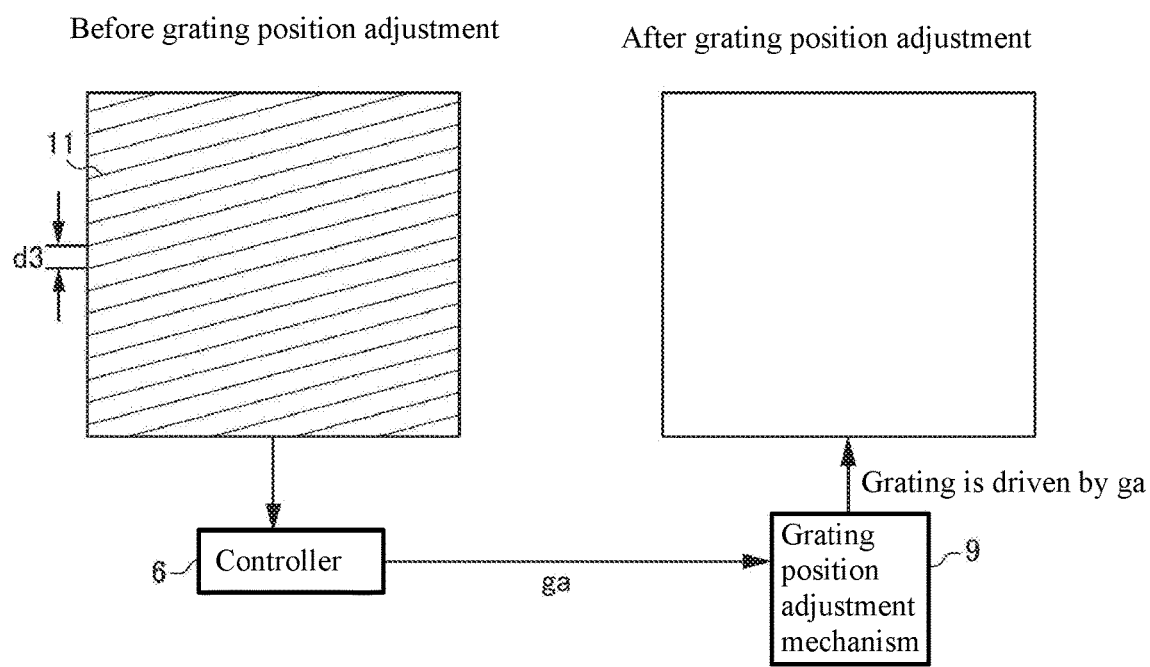
FIG. 5 is a schematic diagram illustrating the position adjustment of the grating by the grating position adjustment mechanism in the X-ray imaging apparatus according to the first embodiment.

Next, referring to FIG. 5, the configuration in which the controller 6 performs the position adjustments of the first grating 2 and the second grating 3 will be described. The example shown in FIG. 5 is a schematic diagram of the image after the first grating 2 and the second grating 3 have been rotated by the grating rotation mechanism 7.

After rotating the grating by the grating rotation mechanism 7, in some cases, the relative position of the first grating 2 among the gratings and the second grating 3 shifts. When the relative position of the first grating 2 among the gratings and the second grating 3 is shifted, a moiré fringe 11 occurs as shown in FIG. 5 (left side—before grating position adjustment) even in the state of performing air imaging without arranging the subject T. In the example shown in FIG. 5, a moiré fringe 11 having a period d3 is generated.

In the first embodiment, the controller 6 is configured to calculate the adjustment amount ga of the grating by the grating position adjustment mechanism 9 based on the moiré fringe 11 generated after rotating the first grating 2 and the second grating 3 by the grating rotation mechanism 7. Specifically, the controller 6 calculates the adjustment amount ga of the grating according to the following equation (1).

$$ga = \frac{1}{2} \cdot \frac{d2}{d3} \cdot s \qquad (1)$$

Here, "ga" is an adjustment amount of the grating. "d2" is a grating pitch of the second grating 3. "d3" is a pitch of the moiré fringe 11. "s" is a pixel size of the detector 4.

The controller 6 is configured to calculate the adjustment amount ga of the grating according to the above equation (1) and rotate the first grating 2 by the calculated adjustment amount ga by the grating position adjustment mechanism 9 to perform the position adjustment between the gratings of the first grating 2 and the second grating 3. After the position adjustment between the gratings of the first grating 2 and the second grating 3, as shown in FIG. 5 (right side), the period of the moiré fringe 11 becomes sufficiently large, and in some cases it almost disappears.

(Switching of Translation Direction of Grating)

Next, with reference to FIG. 6, the configuration in which the controller 6 in the first embodiment switches the direction of the translation of the grating by the grating moving mechanism 8 will be described. In the first example, the image processor 5 generates the dark field image 13 by the fringe scanning method. The fringe scanning method is a method of generating an image based on the detection signal curve (step curve) of the detected X-rays by imaging the grating while translating the grating by one period or more of the grating. In the first embodiment, the grating moving mechanism 8 is configured to translate the first grating 2 by one period (d2) or more of the second grating 3. Further, the grating moving mechanism 8 is configured to change the direction of moving the grating according to the arrangement direction of the first grating 2 and the second grating 3. The grating moving mechanism 8 is configured to move the first grating 2 in a direction in which the translation distance decreases when translating the first grating 2 by one period (d2) or more of the second grating 3.

Specifically, the controller 6 is configured to translate the grating in a direction in which the translational distance becomes smaller among the translational distances calculated by the following equations (2) and (3).

$$swc = \frac{d}{\cos\theta/n} \qquad (2)$$

$$sws = \frac{d}{\sin\theta/n} \qquad (3)$$

Here, "swc" and "sws" are translational distances when translating the grating. "d2" is a pitch of the second grating 3. Further, "θ" is a rotation angle of the grating in a plane (XY plane) orthogonal to the optical axis direction (Z-direction) of the X-rays. Also, "n" is the number (number of steps) of translating the grating.

The translation distance swc of the translation calculated by the above formula (2) is a moving distance when the grating is moved in the vertical direction (Y-direction). The translation distance sws of the translation calculated by the above formula (3) is a moving distance when the grating is moved in the lateral direction (X-direction). The controller 6 calculates the translation distance swc when translating in the lateral direction (X-direction) and the translation distance sws when translating in the vertical direction (Y-direction) and translates the grating in the direction in which the moving distance decreases.

Figure 6A:
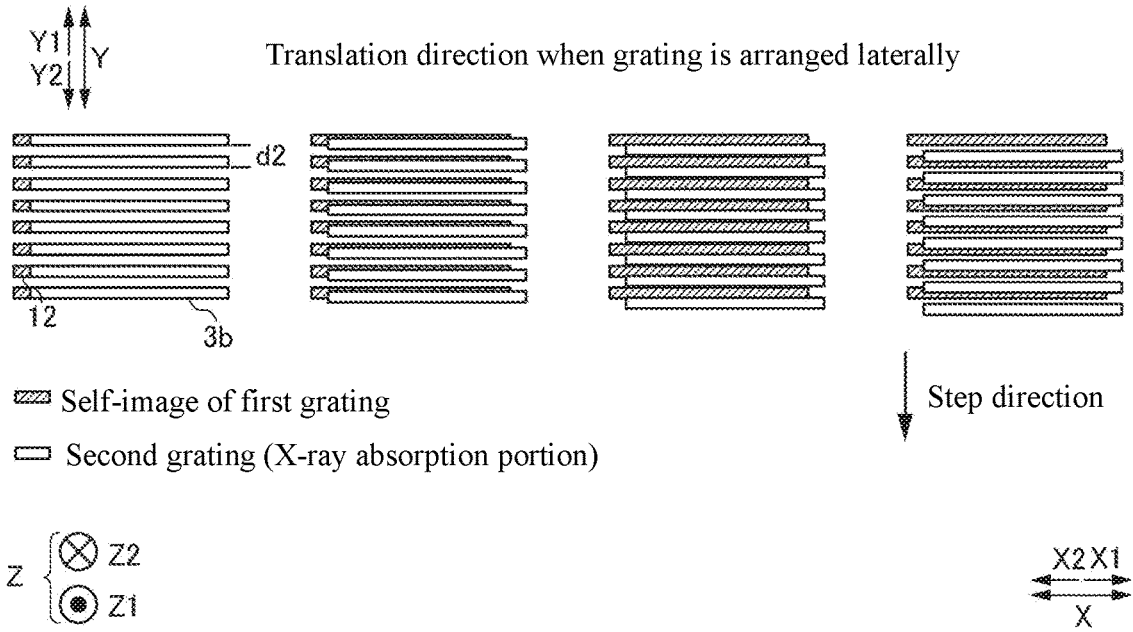
FIG. 6A is a schematic diagram illustrating the movement direction of the grating arranged in a lateral direction by the grating moving mechanism in the X-ray imaging apparatus according to the first embodiment.

The example shown in FIG. 6A is a schematic diagram showing the translation of the grating when the grating is arranged in the lateral direction (X-direction). When the grating is arranged in the lateral direction (X-direction), the controller 6 translates the first grating 2 in the Y2-direction via the grating position adjustment mechanism 9.

Figure 6B:
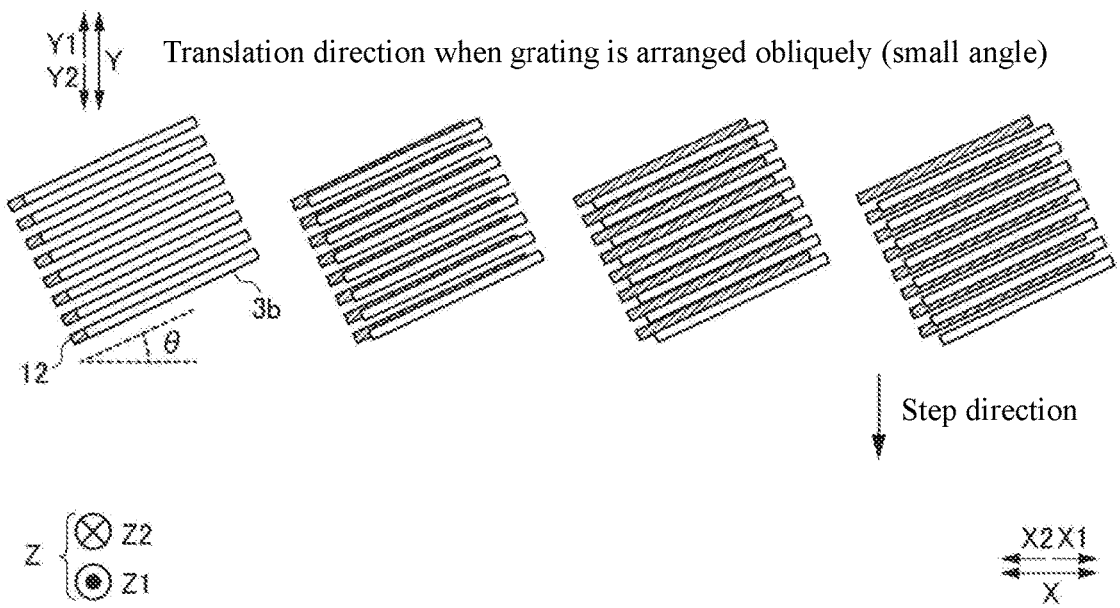
FIG. 6B is a schematic diagram illustrating the moving direction of the grating arranged obliquely by the grating moving mechanism in the X-ray imaging apparatus according to the first embodiment.
Figure 6C:
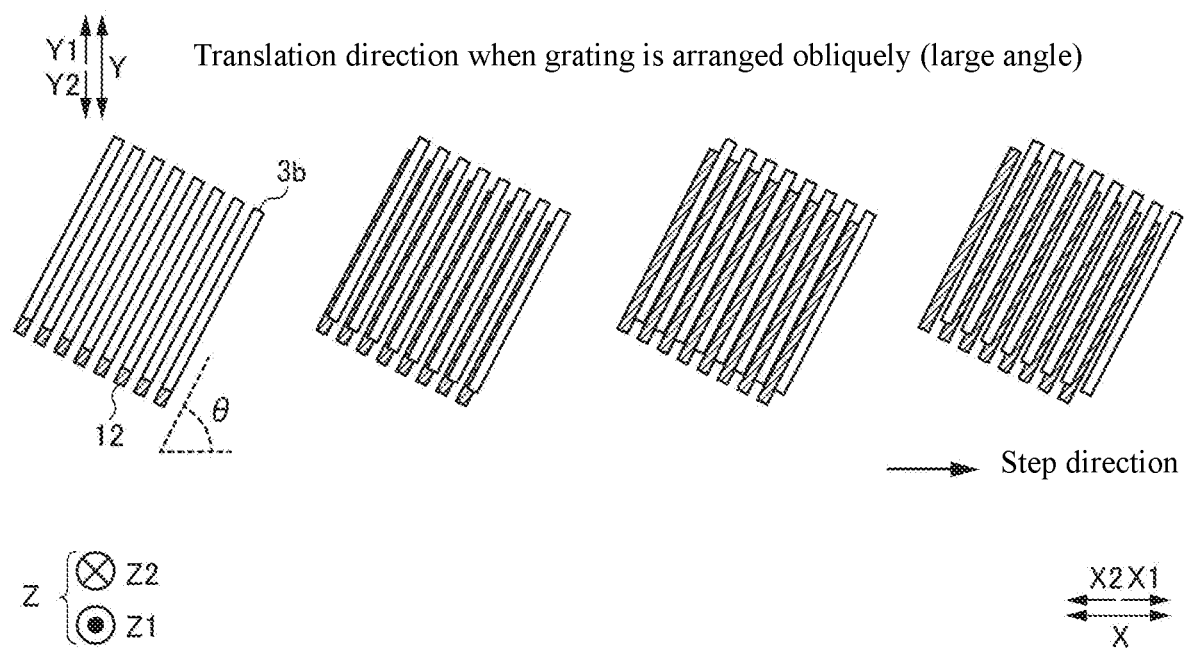
FIG. 6C is a schematic diagram illustrating the moving direction of the grating arranged obliquely at an angle larger than in FIG. 6B by the grating moving mechanism in the X-ray imaging apparatus according to the first embodiment.

The example shown in FIG. 6B is a schematic diagram showing the step direction when the grating is arranged diagonally. FIG. 6B is an example when the grating has a small rotation angle θ. In the example shown in FIG. 6B, the rotation angle θ of the grating is, for example, 30 degrees. When the rotation angle θ of the grating is 30 degrees, the translation distance swc in the vertical direction (Y direction) becomes smaller than the translation distance sws in the lateral direction (X-direction). Therefore, in the example shown in FIG. 6B, the first grating 2 is translated in the vertical direction (Y-direction). The example shown in FIG. 6C is a schematic diagram showing the step direction when the grating is arranged diagonally. FIG. 6C is an example when the grating has a large rotation angle θ. In the example shown in FIG. 6C, the rotation angle θ of the grating is, for example, 60 degrees. When the rotation angle θ of the grating is 60 degrees, the translation distance sws of the lateral direction (X-direction) becomes smaller than the translation distance swc of the vertical direction (Y-direction). Therefore, in the example shown in FIG. 6C, the first grating 2 is translated in the lateral direction (X-direction).

(Imaging of Subject)

Figure 7:
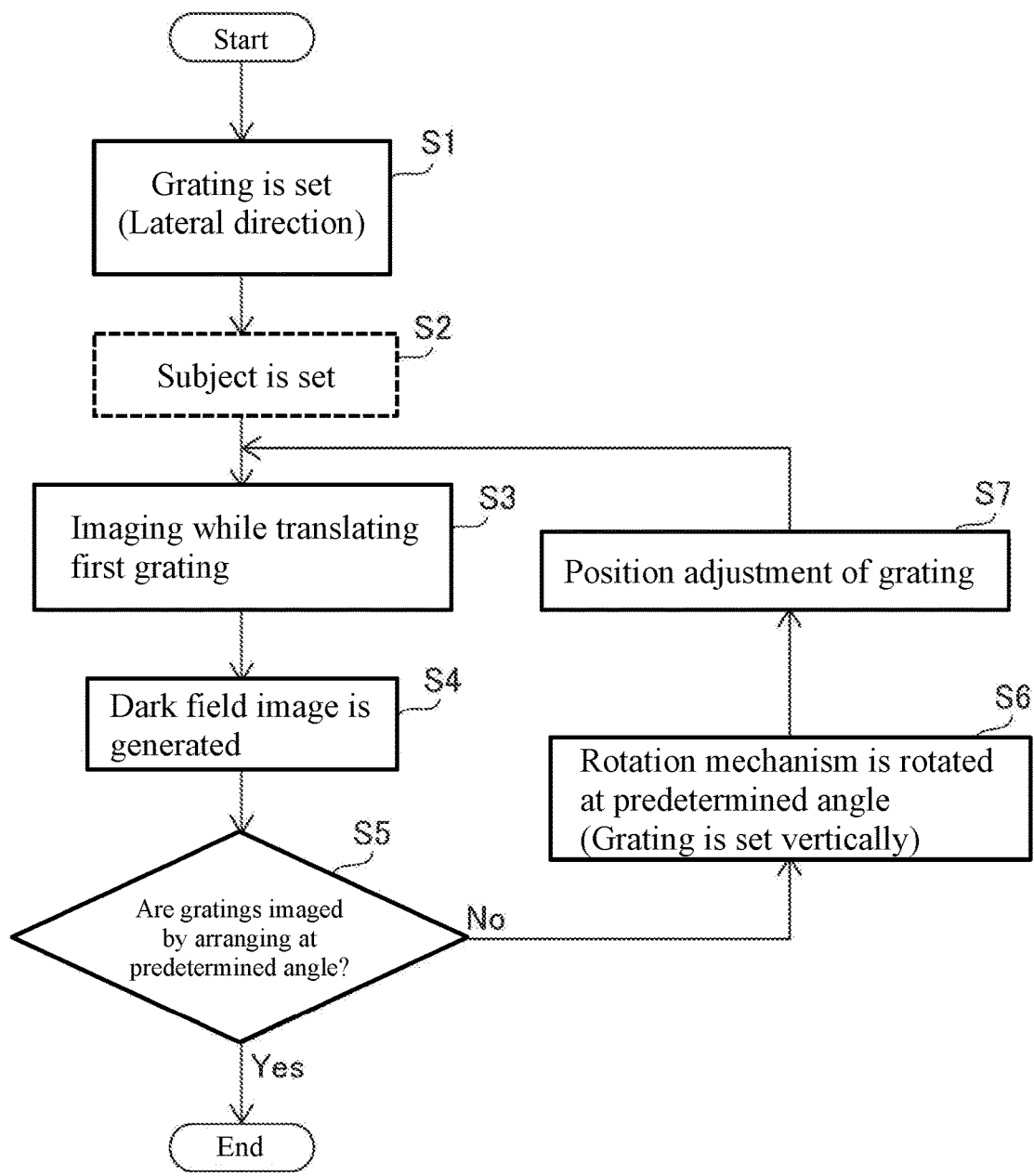
FIG. 7 is a flowchart of an imaging method by the X-ray imaging apparatus according to the first embodiment.

Next, with reference to FIG. 7, the flow of the configuration for imaging the subject T by the X-ray imaging apparatus 100 according to the first embodiment will be described.

In Step S1, the controller 6 arranges the first grating 2 and the second grating 3 laterally (in the X-direction) via the grating rotation mechanism 7. Next, in Step S2, the subject T is arranged by the operator. Note that Step S2 may be performed at any time as long as it is performed before Step S3.

Next, in Step S3, the controller 6 images the subject T while translating the first grating 2 via the grating moving mechanism 8. Next, in Step S4, the image processor 5 generates a dark field image 13 of the subject T.

Next, in Step S5, the controller 6 determines whether or not the first grating 2 and the second grating 3 are imaged at a desired angle. When the first grating 2 and the second grating 3 are not imaged in a state in which they are arranged at a desired angle, the process proceeds to Step S6. When the first grating 2 and the second grating 3 are imaged at a desired angle, the process is terminated.

In Step S6, the controller 6 rotates the first grating 2 and the second grating 3 by a predetermined angle via the grating rotation mechanism 7 to arrange the first grating 2 and the second grating 3 in the vertical direction (Y-direction). In the first embodiment, the predetermined angle is approximately 90 degrees. Next, in Step S7, the controller 6 performs the position adjustment of the first grating 2 via the grating position adjustment mechanism 9. Thereafter, the process proceeds to Step S3.

(Image Generated by Image Processor)

Next, with reference to FIG. 8, an image generated by the image processor 5 according to the first embodiment will be described.

In the first embodiment, the image processor 5 is configured to generate dark field images 13 captured by arranging the first grating 2 and the second grating 3 at a plurality of angles in a plane (XY plane) orthogonal to the optical axis direction (Z-direction). The example shown in FIG. 8 is a dark field images 13 captured by hitting the subject T (CFRP) to form cracks (scratches 14).

Here, the dark field image 13 is an image based on the change of the dose of X-rays for each pixel of the detector 4 caused by the scattering of the X-rays. That is, when X-rays which have passed the grating and detected by the detector are scattered, the scattered X-rays are absorbed by the grating, and therefore the scattered X-rays among the X-rays become undetectable by the detector 4. On the other hand, when X-rays absorbed by the grating are scattered, the scattered X-rays pass through the grating. The X-rays that have scattered and passed through the grating will be detected by the detector 4. Therefore, in the dark field image 13, the dose of X-rays to be detected in each pixel of the detector 4 changes. When the X-rays are scattered in a direction orthogonal to the orientation of the grating, the change of the dose of the X-rays to be detected by the detector 4 becomes remarkable. Scattering of X-rays is caused by multiple refraction of the X-rays by the internal structure (scratches 14) of the subject T. The refraction of X-rays occurs when X-rays pass through the boundary region different in the refractive index. When the X-rays are refracted by the scratch 14, the X-rays are refracted at the boundary between the scratch 14 and the other regions, so that the X-rays are refracted in a direction intersecting with a direction in which the scratch 14 extends. As a result, in the dark field image 13, it is possible to capture the directivity of scattering of the X-rays.

Figure 8A:
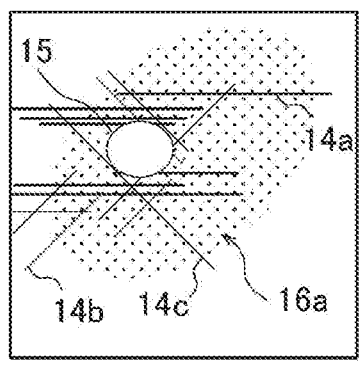
FIG. 8A is a schematic diagram of a dark field image captured by laterally arranging the grating of the X-ray imaging apparatus according to the first embodiment.

FIG. 8A is a dark field image 13a captured by arranging the grating in the lateral direction (see FIG. 3A). In the example shown in FIG. 8A, since the grating is arranged in the lateral direction (X-direction), scratches 14a extending in the lateral direction (X-direction) among the scratches 14 inside the subject T are depicted. Among the scratches 14 inside the subject T, scratches 14b and scratches 14c extending in oblique directions are also depicted. Since the scratches 14b and the scratches 14c extending in oblique directions contain scattering components of X-rays with respect to the lateral direction (X-direction) and the vertical direction (Y-direction), even when the grating is arranged in the lateral direction (X-direction), it is depicted. However, scratches 14b and scratches 14c extending in oblique directions become smaller in the amount of scattering of the X-rays in the vertical direction (Y-direction) when compared with scratches 14a extending in the lateral direction (X-direction), so in the dark field image 13a, it is depicted to be thinner than the scratches 14a extending in the lateral direction (X-direction).

Note that in the dark field image 13a shown in FIG. 8A, the circular area 15 denotes an impact mark caused when hitting the subject T. The distance between layers in the Z-direction of the subject T becomes clogged (reduces) by hitting, and therefore scattering of X-rays becomes weak. Thus, it is depicted in white in the image. Among the dark field image 13a shown in FIG. 8A, the elliptical area 16a (dotted hatched portion) denotes an area depicted by the scattering of the X-rays generated by delamination between layers in the Z-direction within the subject T by giving a hit to the subject T. The elliptical area 16a is an area in which X-rays scattered in the vertical direction (Y-direction) is detected by peeling between layers of the subject T. In the example shown in FIG. 8A, the angle of each grating stored by storage 10 is approximately 0 degrees, and the direction in which the first grating 2 is translated by the grating moving mechanism 8 is the Y-direction.

Figure 8B:
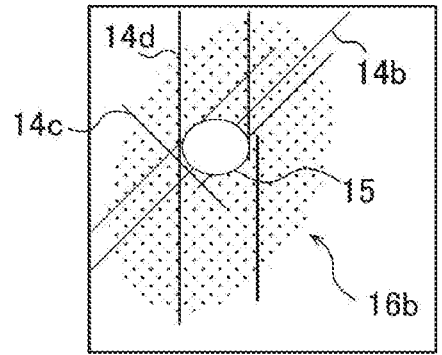
FIG. 8B is a schematic diagram of a dark field image captured by vertically arranging the grating of the X-ray imaging apparatus according to the first embodiment.

FIG. 8B is a dark field image 13b captured by arranging (see FIG. 3C) the grating in the vertical direction (Y-direction). In the example shown in FIG. 8B, since the grating is arranged in the vertical direction (Y-direction), scratches 14d extending in the vertical direction (Y-direction) among scratches 14 inside the subject T are depicted. Further, in the same manner as in the dark field image 13a, among the scratches 14 inside the subject T, scratches 14b and scratches 14c extending in oblique directions are also depicted. The scratches 14b and scratches 14c extending in oblique directions become smaller in the amount of scattering of the X-rays in the lateral direction (X-direction) when compared with scratches 14d extending in the vertical direction (Y-direction), so in the dark field image 13, it is depicted to be thinner than scratches 14d extending in the vertical direction. Note that in the dark field image 13b shown in FIG. 8B, the circular area 15 denotes an impact mark caused when hitting the subject T.

Among the dark field image 13b shown in FIG. 8B, the elliptical area 16b denotes an area depicted by scattering of the X-rays generated by delamination between layers in the Z-direction within the subject T by giving a hit to the subject T. The elliptical area 16b denotes an area in which X-rays scattered in the lateral direction (X-direction) is detected by peeling between layers of the subject T. Therefore, the shape of the elliptical area 16b slightly differs from the shape of the elliptical area 16a shown in FIG. 8A. Although not shown, when each grating is arranged obliquely as shown in FIG. 3B, a scratch 14c extending in a direction along the grating direction is depicted. However, the scratch 14b extending in a direction orthogonal to the direction of the grating is not depicted.

Since the scratch 14a and the scratch 14d each extend in an oblique direction with respect to the grating, they are depicted to be thinner than the scratch 14c in the dark field image 13. In the example shown in FIG. 8B, the angle of each grating stored by storage 10 is approximately 90 degrees, and the direction in which the first grating 2 is translated by the grating moving mechanism 8 is the X-direction.

(Effects of First Embodiment)

In the first embodiment, the following effects can be obtained.

In the first embodiment, as described above, the X-ray imaging apparatus 100 is provided with the X-ray source 1, the plurality of gratings including the first grating 2 for forming the self-image 12 by the X-rays irradiated from the X-ray source 1 and the second grating 3 for interfering with the self-image 12 of the first grating 2, the detector 4 configured to detect the X-rays irradiated from the X-ray source 1, the grating rotation mechanism 7 for rotating the plurality of gratings respectively in a plane (XY plane) orthogonal to the optical axis direction (Z-direction) of the X-ray, and the image processor 5 configured to generate at least a dark field image 13 from the intensity distribution of the X-ray detected by the detector 4. The image processor 5 is configured to generate dark field images 13 captured by arranging the grating at a plurality of angles in a plane (XY plane) orthogonal to the optical axis direction (Z-direction).

Thus, by changing the orientation of the grating, it is possible to change the orientation of the subject T with respect to the grating without changing the orientation of the subject T with respect to the grating. Therefore, it is possible to image the internal structure (scratch 14) of the subject T without changing the orientation of the subject T with respect to the grating. Further, since it is possible to image the internal structure (scratch 14) of the subject T without changing the orientation of the subject T with respect to the grating, for example, even in the case of comparing the dark field images 13 captured by arranging the grating at a plurality of angles, it is not necessary to match the orientation of the subject T in each image, which enables easy comparison of each image.

In addition, in the first embodiment, as described above, the grating rotation mechanism 7 is configured to arrange a plurality of gratings in the vertical direction (Y-direction) and the lateral direction (X-direction) among the vertical direction (Y-direction), the lateral direction (X-direction), and the oblique direction in a plane (within the XY plane) orthogonal to the optical axis direction (Z-direction). As a result, when the grating is rotated, it is possible to rotate the plurality of gratings so that the orientation of the grating with respect to the orientation of the subject T is different. As a result, within the subject T, internal structures (scratches 14) different in the scattering direction of X-rays can be imaged, respectively.

Further, in the first embodiment, as described above, the X-ray imaging apparatus 100 further includes the grating moving mechanism 8 for moving the first grating 2. The grating moving mechanism 8 is configured to move the first grating 2 together with the grating rotation mechanism 7 after rotating a plurality of gratings. Thus, even in cases where the first grating 2 is moved after rotating the first grating 2 and the second grating 3, the first grating 2 can be moved without rotating the grating moving mechanism 8.

Further, in the first embodiment, as described above, the grating moving mechanism 8 is configured to move the grating in the vertical direction (Y-direction) or the lateral direction (X-direction) in a plane (XY plane) orthogonal to the optical axis direction (Z-direction), also change the direction of moving the grating according to the arrangement direction of the plurality of gratings, and move the first grating 2 in a direction in which the translation distance decreases when translating the first grating 2 by one period (d2) or more of the second grating 3.

With this, even in cases where the grating is translated by arranging at a plurality of angles, the grating can be translated in the direction that the translation distance of the grating decreases depending on the arrangement direction of the grating. As a result, the deterioration of the image quality of the image due to errors at the time of the translation can be suppressed.

Further, in the first embodiment, as described above, the grating rotation mechanism 7 includes the grating holder 70 for holding the grating and the rotating section 71 for rotating the grating holder 70. With this, for example, as compared with the case where the grating is rotated together with the grating moving mechanism 8, since the grating holder 70 is rotated by the rotating section 71, the grating rotation mechanism 7 can be downsized. Further, since the grating can be rotated by the grating rotation mechanism 7, the mechanism for rotating the grating moving mechanism 8 in accordance with the rotation of the grating becomes unnecessary, so that it is possible to simplify the device configuration by that.

Further, in the first embodiment, as described above, the grating position adjustment mechanism 9 for adjusting the relative position of the first grating 2 among the plurality of gratings is further provided, and the grating rotation mechanism 7 is configured to be held on the grating moving mechanism 8 via the grating position adjustment mechanism 9. With this, even when the grating is rotated by the grating rotation mechanism 7, the position adjustment of the grating and the movement of the grating can be performed without rotating the grating position adjustment mechanism 9 and the grating moving mechanism 8. As a result, it becomes unnecessary to rotate the grating position adjustment mechanism 9 and the grating moving mechanism 8 in accordance with the rotation of the grating, so that it is possible to suppress complication of the apparatus configuration.

Further, in the first embodiment, as described above, the X-ray imaging apparatus 100 is further provided with the controller 6 for calculating the adjustment amount ga of the grating by the grating position adjustment mechanism 9 based on the moiré fringe 11 generated after rotating the plurality of gratings by the grating rotation mechanism 7. With this, even if the displacement of the relative position among the plural gratings occurs by rotating the grating, it is possible to calculate the adjustment amount ga of the grating based on the moiré fringe 11, so that it is possible to easily perform the position adjustment of the grating.

Further, in the first embodiment, as described above, storage 10 for storing the angle information of the plurality of gratings rotated by the grating rotation mechanism 7 is further provided. This makes it easy to grasp the direction of the scattered component during the image analysis.

Second Embodiment

Figure 9:
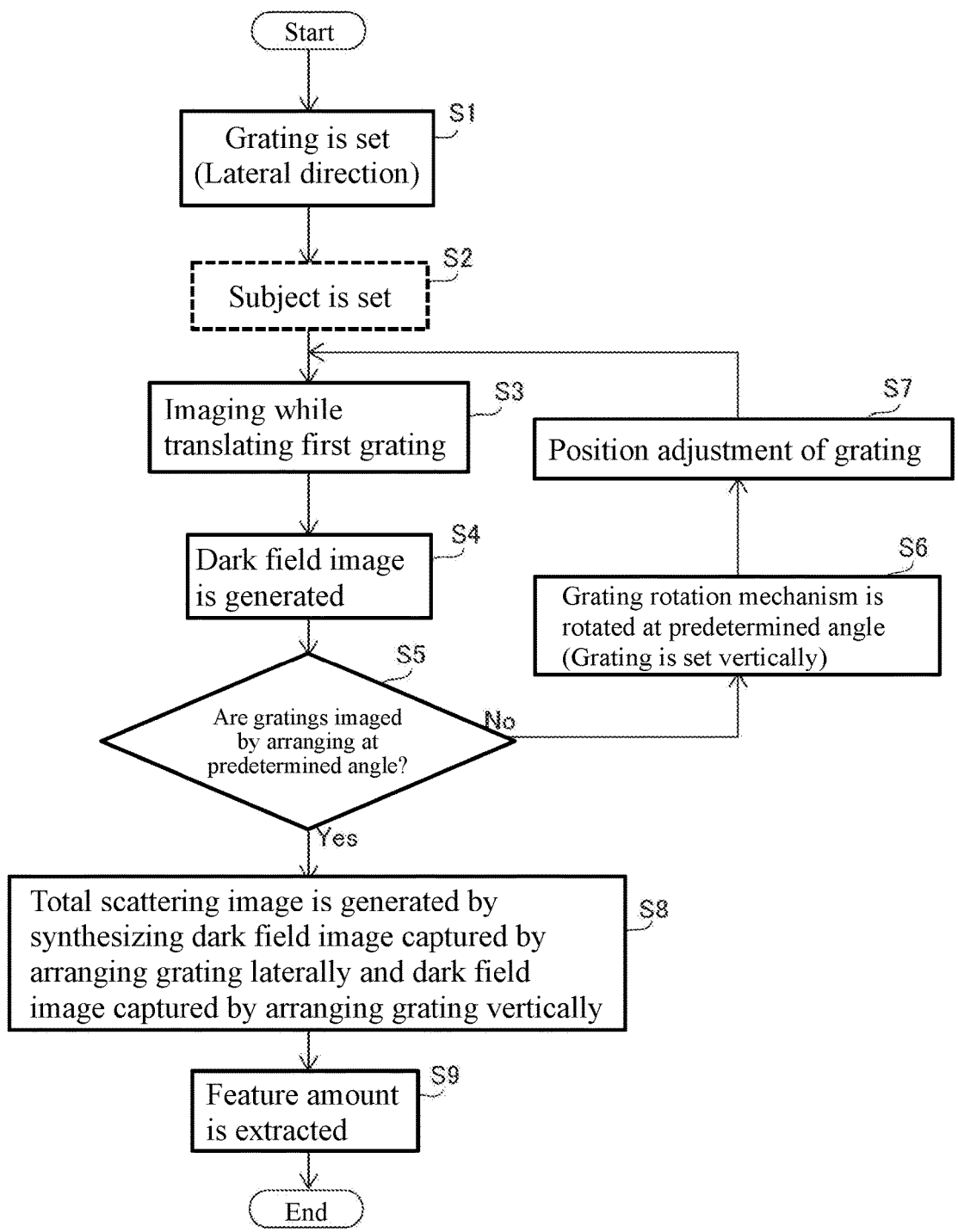
FIG. 9 is a flowchart of an imaging method by an X-ray imaging apparatus according to a second embodiment.

Next, with reference to FIG. 1, FIG. 9, and FIG. 10, an X-ray imaging apparatus 200 (see FIG. 1) according to a second embodiment will be described. Unlike the first example in which the dark field image 13 is generated from images captured by arranging the grating in the lateral direction (X-direction) and the vertical direction (Y-direction), in the second embodiment, the image processor 5 is configured to generate a total scattering image (see FIG. 10C) representing the intensity of scattering of the X-rays by the subject T by synthesizing a plurality of dark field images 13 captured by arranging the gratings at a plurality of angles in a plane (XY plane) orthogonal to the optical axis direction (Z-direction). Note that the total scattering image 20 denotes an image obtained by imaging the scattering of X-rays in all directions caused by the subject T. The same reference numerals are allotted to the same configurations as those of the first embodiment, and the description thereof will be omitted.

(Configuration of X-Ray Imaging Apparatus)

First, with reference to FIG. 1, the configuration of an X-ray imaging apparatus 200 according to a second embodiment will be described.

In the second embodiment, the image processor 5 is configured to generate a total scattering image 20 representing the intensity of scattering of the X-rays by the subject T by synthesizing a plurality of dark field images 13 captured by arranging the grating at a plurality of angles in a plane (XY plane) orthogonal to the optical axis direction (Z-direction).

Specifically, the image processor 5 is configured to synthesize the dark field images 13a captured by arranging the grating in the lateral direction (X-direction) and the dark field image 13b captured by arranging the grating in the vertical direction (Y-direction) to generate a total scattering image 20. In the second embodiment, the image processor 5 is configured to acquire the information on the internal structure (scratch 14) having a directivity within the subject T as the feature amount of the subject T, and the information on the internal structure (scratch 14) having a directivity in the subject T includes at least the length L of the scratch 14a (see FIG. 10C) and the width W of the scratch 14d (see FIG. 10C). Note that the length L of the scratch 14a and the width W of the scratch 14d are an example of the "length of the internal structure having a directivity" and an example of the "width of the internal structure having a directivity", respectively.

(Imaging Method of Subject)

Next, with reference to FIG. 9, the flow of the method of imaging the subject T by the X-ray imaging apparatus 200 according to the second embodiment will be described. The description of Steps similar to those of the first embodiment will be omitted.

In Step S1 to Step S7, a plurality of dark field images 13 captured by arranging each grating at a desired angle is generated. Thereafter, the process proceeds to Step S8.

In Step S8, the image processor 5 synthesizes the dark field image 13a captured by arranging the first grating 2 and the second grating 3 in a lateral direction (X-direction) and the dark field image 13b captured by arranging the first grating 2 and the second grating 3 in the vertical direction (Y-direction) to generate a total scattering image 20.

Next, in Step S9, the image processor 5 extracts the feature amount of the internal structure (scratch 14) of the subject T from the synthesized total scattering image 20.

(Image Generated by Image Processor)

Next, with reference to FIG. 10, an image generated by the image processor 5 according to the second embodiment will be described.

Figure 10A:
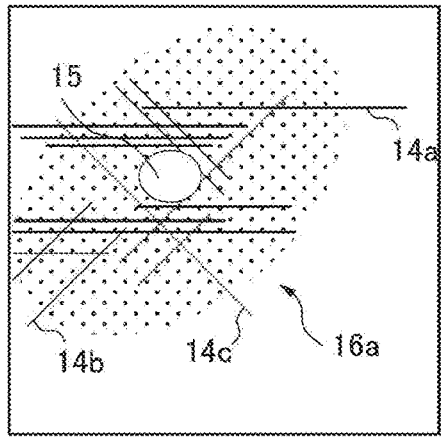
FIG. 10A is a schematic diagram of a dark field image captured by laterally arranging the grating of the X-ray imaging apparatus according to the second embodiment.
Figure 10B:
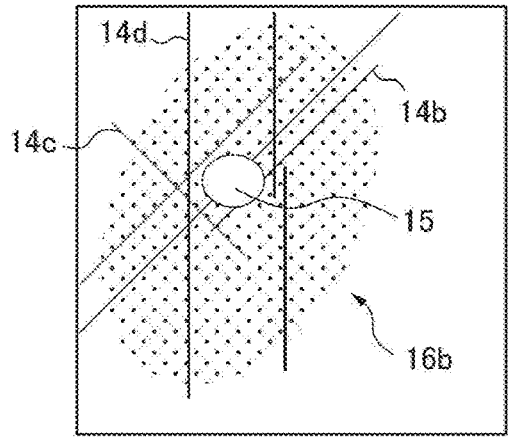
FIG. 10B is a schematic diagram of a dark field image captured by vertically arranging the grating of the X-ray imaging apparatus according to the second embodiment.

FIG. 10A and FIG. 10B are schematic diagrams similar to those shown in FIG. 8A and FIG. 8B, respectively, and therefore the description thereof will be omitted. FIG. 10C is a schematic diagram of a total scattering image 20 obtained by synthesizing the dark field image 13a captured by arranging the grating in the lateral direction (X-direction) and the dark field image 13b captured by arranging the grating in the vertical direction. As the synthesis method, any method may be used. In the second embodiment, the image processor 5 is configured to generate the total scattering image 20 by the dark field image 13a shown in FIG. 10A, the dark field image 13b shown in FIG. 10B, and the following expression (4).

$$I^{dark}(x, y) = \sum_{k=1}^{M} I_k^{dark}(x, y) \quad (4)$$

Here, $I^{dark}_k(x, y)$ is a dark field image 13. Also, "k" is the number representing each of the plurality of dark field images 13 captured by changing the orientation of the grating, and "M" is the total number (number of sheets) of the captured dark field images 13. In the second embodiment, for example, M=2. "x" and "y" are position coordinates of pixels in the X-direction and Y-direction, respectively, in the image.

Figure 10C:
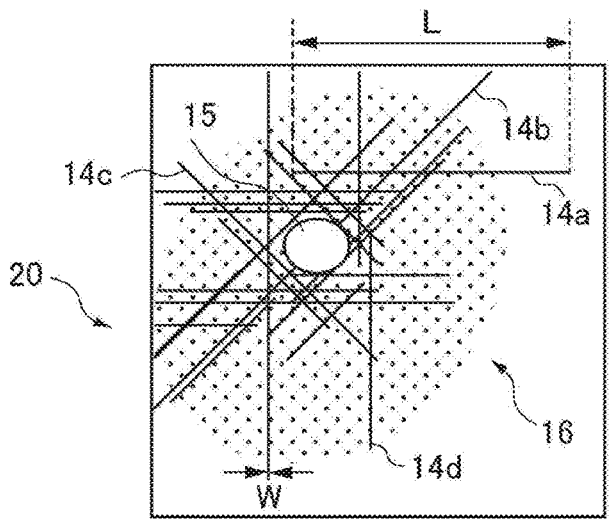
FIG. 10C is a dark field image obtained by synthesizing a dark field image captured by vertically arranging the grating and a dark field image captured by laterally arranging the grating.

Among the total scattering image 20 shown in FIG. 10C, the elliptical area 16 (dotted hatched portion) denotes an area depicted by scattering of the X-rays generated by delamination between layers in the Z-direction within the subject T by giving a hit to the subject T. The elliptical area 16 is an area in which X-rays scattered in the vertical direction (Y-direction) and the lateral direction (X-direction) are detected by peeling between layers of the subject T.

The other configurations of the second embodiment are the same as those of the first embodiment.

(Effects of Second Embodiment)

In the second embodiment, the following effects can be obtained.

In the second embodiment, as described above, the image processor 5 is configured to synthesize a plurality of dark field images 13 captured by arranging the grating at a plurality of angles in a plane (XY plane) orthogonal to the optical axis direction (Z-direction). Here, since the dark field image 13 is captured based on the scattering of the X-rays in the subject T, the sensitivity varies depending on the orientation of the grating (some scattered image cannot be imaged).

By configuring as described above, it is possible to obtain an all-directional scattering image supplementing the sensitivity difference of scattering of the X-rays by the total scattering image 20 generated by synthesizing a plurality of dark field images 13 in which the X-rays are scattered in a plurality of directions. Further, it is possible to image the subject T without changing the orientation of the subject, and therefore a total scattering image 20 can be generated without performing the positional adjustment of the subject T. As a result, it is possible to easily and accurately generate the total scattering image 20.

Further, in the second embodiment, as described above, the image processor 5 is configured to acquire the feature amount of the subject T from the image (total scattering image 20) generated by synthesizing the plurality of dark field images 13. With such a configuration, it is possible to precisely synthesize the images without performing the positional adjustment, which makes it possible to easily and highly accurately acquire the feature amount.

Further, in the second embodiment, as described above, the image processor 5 is configured to acquire the information on the internal structure (scratch 14) having a directivity within the subject T as the feature amount of the subject T, and the information on the internal structure (scratch 14) having a directivity in the subject T includes at least the length L of the scratch 14a and the width W of the scratch 14d. With this structure, the shape of the internal structure (scratch 14) having a directivity such as the internal structure (scratch 14) of the carbon fiber reinforced plastic (CFRP) can be grasped in more detail.

Third Embodiment

Next, with reference to FIG. 1, and FIG. 11 to FIG. 14, an X-ray imaging apparatus 300 (see FIG. 1) according to a third embodiment will be described. Unlike the second embodiment in which a total scattering image 20 of the subject T is generated, in the third embodiment, the image processor 5 (see FIG. 1) is configured to generate at least either one of the scattering oriented image 22 (see FIG. 13) representing the directivity of scattering of the X-rays by the subject T and the directivity intensity image 23 (see FIG. 14) representing the strength of the directivity of scattering of the X-rays by the subject T using a plurality of dark field images 13 different in the angle of the plurality of gratings.

Note that the scattering oriented image 22 denotes an image obtained by imaging each of the internal structures of the subject T based on the direction in which X-rays are scattered by the dark field image 13 captured by changing the orientation of the grating with respect to the subject T. The directivity intensity image 23 denotes an image formed based on the strength of the scattering directivity of X-rays of each of the internal structure of the subject T. The same reference numerals are allotted to the same configurations as those of the first embodiment and the second embodiment, and the description thereof will be omitted.

(Configuration of X-Ray Imaging Apparatus)

First, with reference to FIG. 1, the configuration of the X-ray imaging apparatus 300 according to the third embodiment will be described.

In the third embodiment, the image processor 5 is configured to generate at least either one of the scattering oriented image 22 representing the directivity of scattering of the X-rays by the subject T and the directivity intensity image 23 representing the strength of the directivity of scattering of the X-rays by the subject T using a plurality of dark field images 13 different in the angle of the plurality of gratings. Specifically, the image processor 5 is configured to generate either one of the scattering oriented image 22 and the directivity intensity image 23 based on a plurality of dark field images 13 (see FIG. 12A to FIG. 12 D) captured by arranging the grating at 0, 45, 90, and 135 degrees. In the third embodiment, an example in which both the scattering oriented image 22 and the directivity intensity image 23 are generated.

(Imaging Method of Subject)

Figure 11:
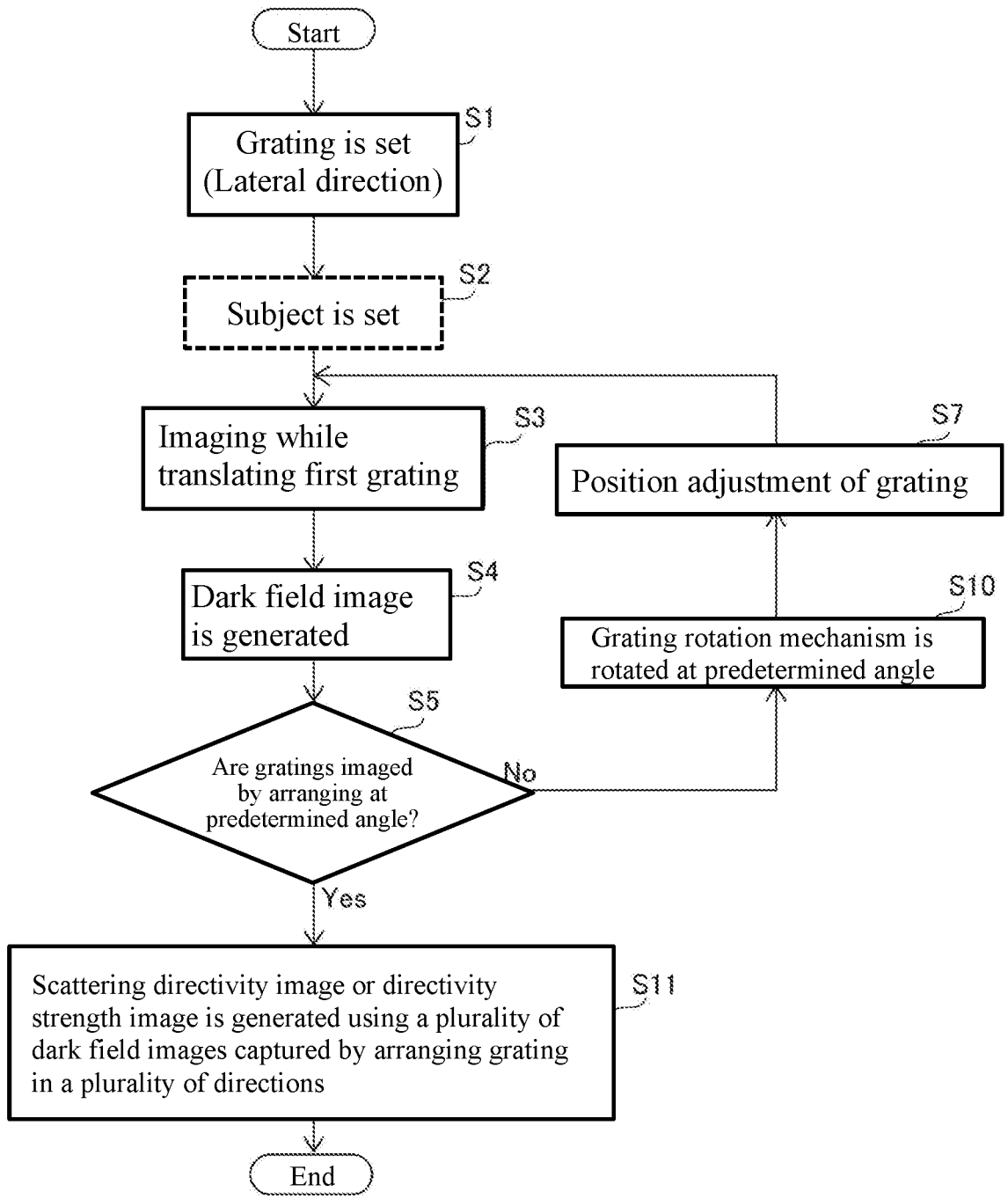
FIG. 11 is a flowchart of an imaging method by an X-ray imaging apparatus according to a third embodiment.
Figure 12A:
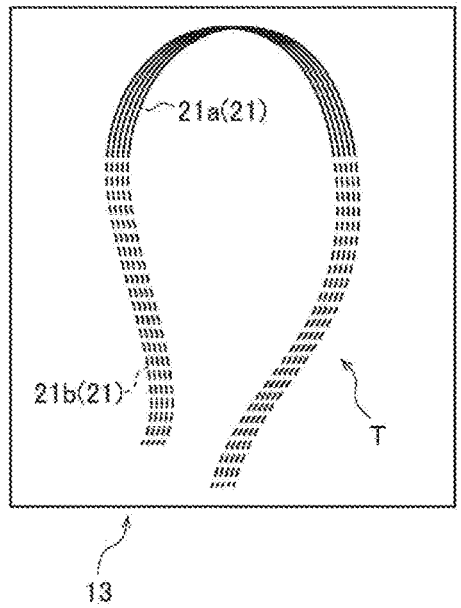
FIG. 12A is a schematic diagram of a dark field image captured by arranging the grating according to the third embodiment at an angle of 0 degrees.
Figure 12B:
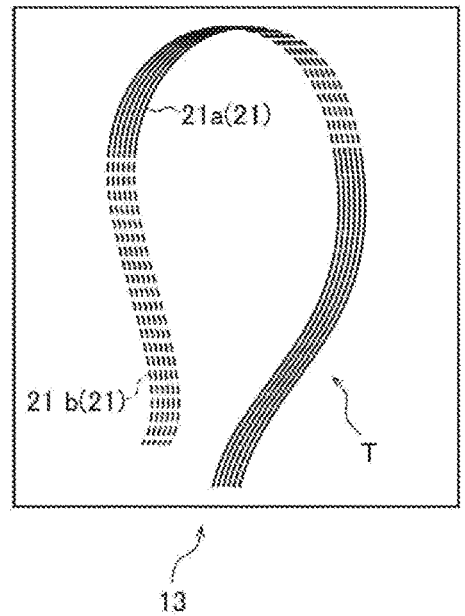
FIG. 12B is a schematic diagram of a dark field image captured by arranging the grating according to the third embodiment at an angle of 45 degrees.
Figure 12C:
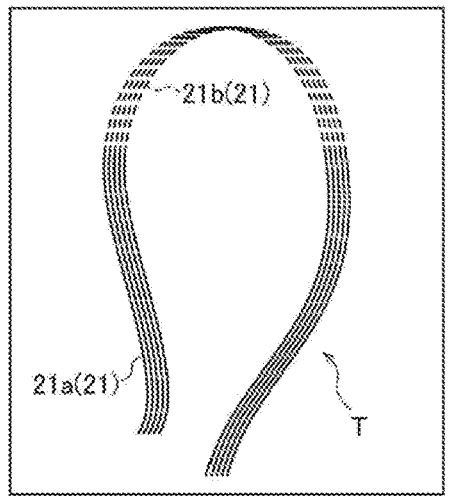
FIG. 12C is a schematic diagram of a dark field image captured by arranging the grating according to the third embodiment at an angle of 90 degrees.
Figure 12D:
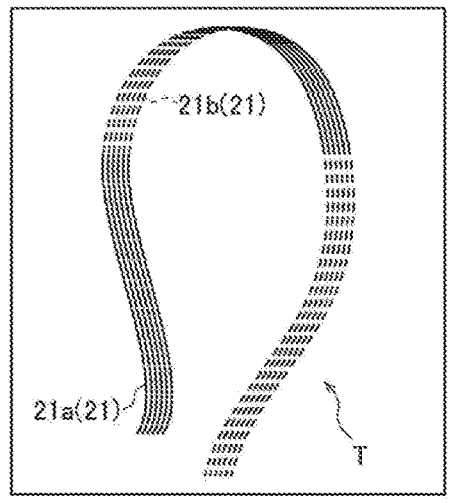
FIG. 12D is a schematic diagram of a dark field image captured by arranging the grating according to the third embodiment at an angle of 135 degrees.

Next, with reference to FIG. 11, the flow of the method of imaging the subject T by the X-ray imaging apparatus 300 according to the second embodiment will be described. The description of Steps similar to those of the first and second embodiments will be omitted.

In Step S1 to Step S5, Step S10, and Step S7, a plurality of imaged dark field images 13 captured by arranging each grating at a desired angle is generated. Thereafter, the process proceeds to Step S11. In the processing of Step S10, unlike the processing in Step S6 of the first and second embodiments, the controller 6 rotates the grating to 0 degrees, 45 degrees, 90 degrees, and 135 degrees via the grating rotation mechanism 7.

In Step S11, the image processor 5 generates the scattering oriented image 22 or the directivity intensity image 23 based on a plurality of dark field images 13 captured by arranging the first grating 2 and the second grating 3 at 0, 45, 90, and 135 degrees.

(Image Generated by Image Processor)

Next, with reference to FIG. 12 to FIG. 14, an image generated by the image processor 5 according to the third embodiment will be described.

FIG. 12A to FIG. 12D are schematic diagrams of a dark field image 13 captured by arranging the grating in different orientations. Specifically, FIG. 12A to FIG. 12D are dark field images 13 captured in a state in which the grating is arranged at 0 degrees, 45 degrees, 90 degrees, and 135 degrees, respectively. In the third embodiment, as a subject T, an example is shown in which a fiber bundle obtained by bundling a plurality of fibers 21 is imaged. The example shown in FIG. 12 is an example of imaging the subject T arranged in a state of being bent in an annular shape. Since the subject T is bent in a circular shape, in the subject T, there are areas where the orientation of the fiber 21 with respect to the grating is different. When the orientation of the fiber 21 with respect to the grating is different, since the sensitivity of scattering of the X-rays is different, the way of reflection in the dark field image 13 is different. The sensitivity of scattering of the X-rays becomes stronger when scattering the X-rays in a direction approximately orthogonal to the extending direction of the grating. In FIG. 12, among the fibers 21 in the subject T, the fibers 21 arranged in the direction in which the scattering sensitivity of X-rays becomes strong is shown by solid lines as the fibers 21a. Further, the fibers 21 arranged in the direction in which the sensitivity of scattering of the X-rays is weakened are indicated by broken lines as the fibers 21b.

In the third embodiment, the image processor 5 generates a scattering oriented image 22 or a directivity intensity image 23 based on the plurality of dark field images 13 shown in FIG. 12. Specifically, the center of the dark field image 13 imaged in a plurality of grating directions on a complex plane is defined as the following equation (5).

$$S^{dark}(x, y) = \sum_{k=1}^{M} I_k^{dark}(x, y)\exp\left(-\frac{2i\pi k}{M}\right) \quad (5)$$

Here, "$S^{dark}(x, y)$" is a center of the dark field image 13 imaged in a plurality of grating directions on a complex plane, and "k" corresponds to the identification number in each grating direction.

The image processor 5 is configured to generate a scattering oriented image 22 or a directivity intensity image 23 on the basis of the aforementioned equations (4) and (5), and the following equations (6) and (7).

$$\varphi^{dark}(x, y) = \arg[S^{dark}(x, y)] \quad (6)$$

$$V^{dark}(x, y) = \frac{2|S^{dark}(x, y)|}{I^{dark}(x, y)} \quad (7)$$

Here, $\varphi^{dark}(x, y)$ is an expression indicating the direction of scattering of the X-rays. The equation (6) is acquiring the phase information when $I^{dark}k$ is a function of k, which corresponds to the directivity of scattering. Further, $V^{dark}(x, y)$ is an expression indicating the strength of the scattering directivity of X-rays. The equation (7) normalizes the amplitude with the average value when $I^{dark}k$ is a function of k, which corresponds to the strength of directivity. Note that the direction of scattering of the X-rays is mainly in which direction to scatter X-rays. In addition, the strength of directivity of scattering of X-rays shows bias in the direction of scattering the X-rays, and as the scattering directivity of X-rays is stronger, X-rays are scattered in a specific direction. Further, the weaker the scattering directivity of X-rays is, the more X-rays are scattered isotropically.

Here, in the scattering oriented image 22, when the direction of scattering of the X-rays is represented by the difference (gray scale) of the pixel value, it is sometime difficult to grasp at a glance which pixel value is scattering X-rays in which direction. Therefore, in the third embodiment, the image processor 5 is configured to generate a scattering oriented image 22 displaying the directivity of scattering of the X-rays and the color in an associated manner. As a method of displaying the directivity of scattering of the X-rays and the color in an associated manner, for example, there is a method of representing the directivity (0 degree to 359 degrees) in a manner associated with each color of a hue circle (cyclic change in hue). When expressing the directivity in a manner associated with each color of a hue circle, a user can grasp the angle of directivity by analogizing the position of the corresponding color in a hue circle. In the example shown in FIG. 13, the directivity of scattering and the type of line indicating the fibers 21 are shown in an associated manner for convenience.

Figure 13:
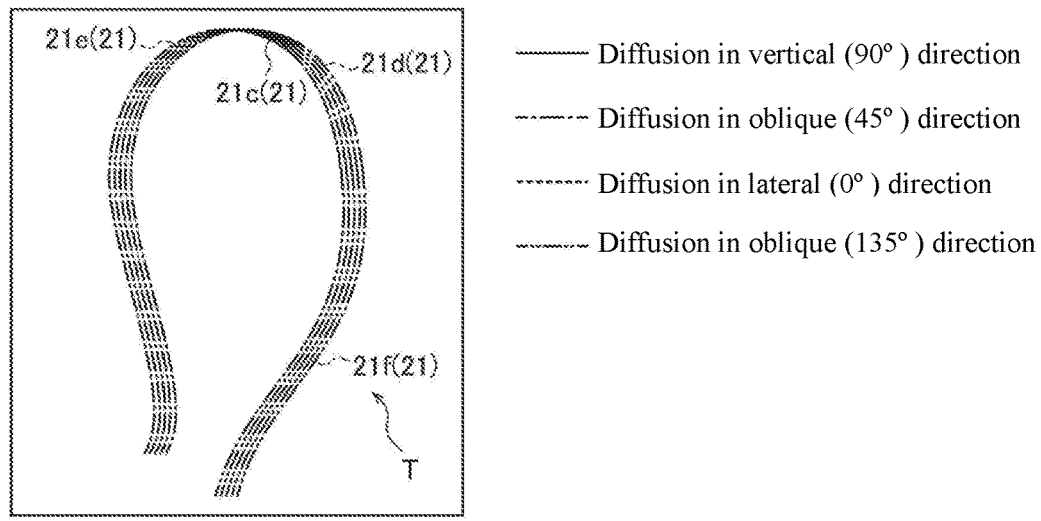
FIG. 13 is a schematic diagram of a scattering oriented image generated by the image processor according to the third embodiment.

That is, in FIG. 13, among the fibers 21 contained in the subject T, the fibers 21 scattering the X-rays in the vertical (90 degrees) direction are illustrated by solid lines as the fibers 21c. Among the fibers 21 contained in the subject T, the fibers 21 scattering X-rays in an oblique direction (45 degrees) are shown by dashed lines as the fibers 21d. Further, among the fibers 21 contained in the subject T, the fibers 21 scattering X-rays in a lateral direction (0 degrees) are shown by dashed lines as the fibers 21e. Further, among the fibers 21 contained in the subject T, the fibers 21 scattering X-rays in an oblique direction (135 degrees) are shown by two-dot chain lines as the fibers 21f.

Figure 14:
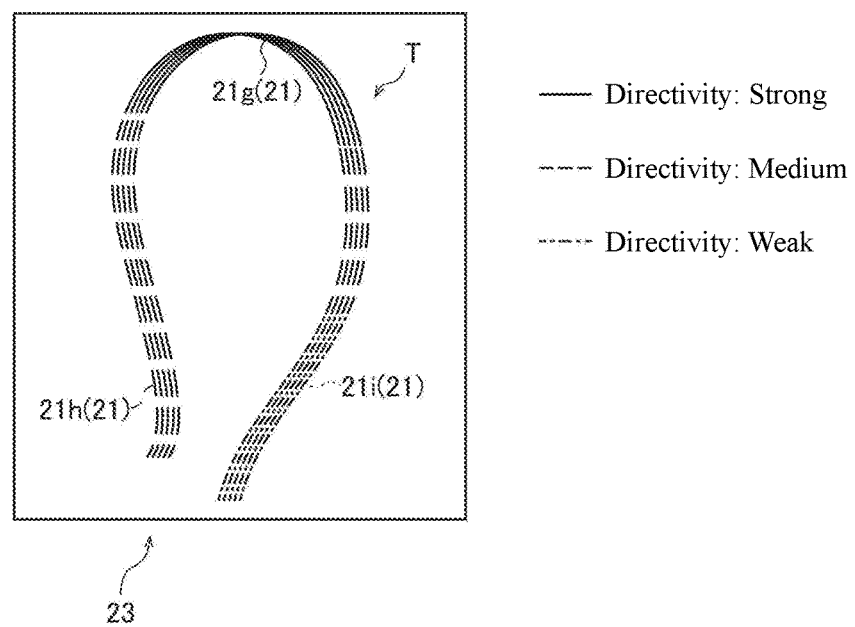
FIG. 14 is a schematic diagram of the directivity intensity image generated by the image processor according to the third embodiment.

In the example shown in FIG. 14, in the directivity intensity image 23, the strength of the directivity is illustrated in association with the type of the line indicating the fiber 21. That is, among the fibers 21 contained in the subject T, the fiber 21 strong in the directivity of scattering of the X-rays is illustrated by solid lines as the fibers 21g. Further, among the fibers 21 contained in the subject T, the fiber 21 medium in the directivity of scattering of the X-rays is illustrated broken lines as the fibers 21h. Further, among the fibers 21 contained in the subject T, the fiber 21 weak in the directivity of scattering of the X-rays is illustrated by dot-dash lines as the fibers 21i.

The other configurations of the third embodiment are the same as those of the first and second embodiments.

(Effects of Third Embodiment)

In the third embodiment, the following effects can be obtained.

In the third embodiment, as described above, the image processor 5 is configured to further generate at least either one of the scattering oriented image 22 representing the directivity of scattering of the X-rays by the subject T and the directivity intensity image 23 representing the strength of the directivity of scattering of the X-rays by the subject T using a plurality of dark field images 13 different in the angle of the plurality of gratings. With this, by generating the scattering oriented image 22, it is possible to grasp the scattering of the X-rays by the subject T. Further, by generating the directivity intensity image 23, the intensity of the directivity of scattering of the X-rays by the subject T can be grasped. As a result, it is possible to grasp the distribution of a plurality of the internal structures (fibers 21) in which the directivity of the scattering is different within the subject T, the distribution of defects occurred in the subject T, and the like in more detail.

Further, in the third embodiment, as described about, the image processor 5 is configured to generate the scattering oriented image 22 displaying the directivity of scattering of the X-rays and the color in an associated manner. With this configuration, in the scattering oriented image 22, the directivity of scattering of the X-rays and the color are associated with each other. Therefore, for example, compared with the scattering oriented image 22 in which the difference of directivity is displayed by the pixel value difference (brightness of the image), it is possible to easily grasp the directivity of scattering of the X-rays.

The other effects of the third embodiment are the same as those of the first and second embodiments.

Fourth Embodiment

Next, with reference to FIG. 1, FIG. 15, and FIG. 16, an X-ray imaging apparatus 400 (see FIG. 1) according to a fourth embodiment will be described. Unlike the first embodiment in which the grating rotation mechanism 7 includes a gear-like grating holder 70 and a gear-like rotating section 71, in the fourth embodiment, the grating rotation mechanism 7 is configured by a belt-pulley mechanism in which a grating holder 70 and a rotating section 71 are connected by a belt 74. The grating holder 70 includes, for example, a toothed pulley. The rotating section 71 includes, for example, a pinion. The belt 74 includes, for example, a timing belt. The same reference numerals are allotted to the same configurations as those of the first to third embodiments, and the description thereof will be omitted.

(Configuration of Grating Rotation Mechanism)

Figure 15:
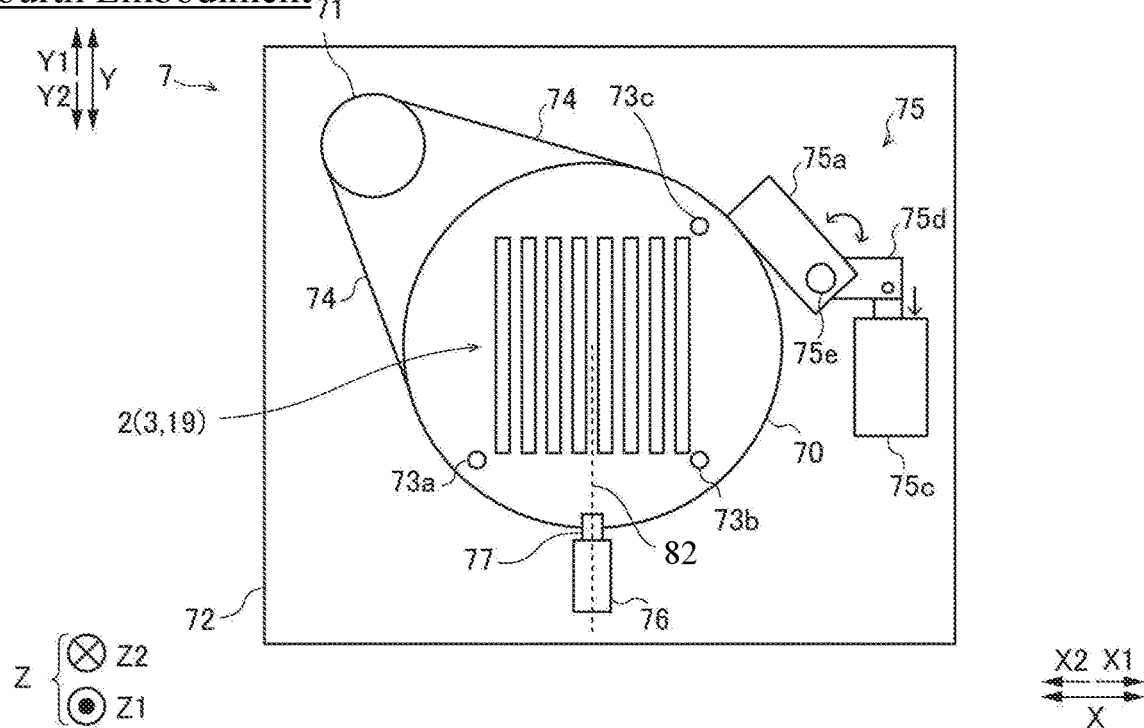
FIG. 15 is a schematic diagram of the grating rotation mechanism of an X-ray imaging apparatus according to a fourth embodiment as viewed from the Z1-direction.
Figure 16:
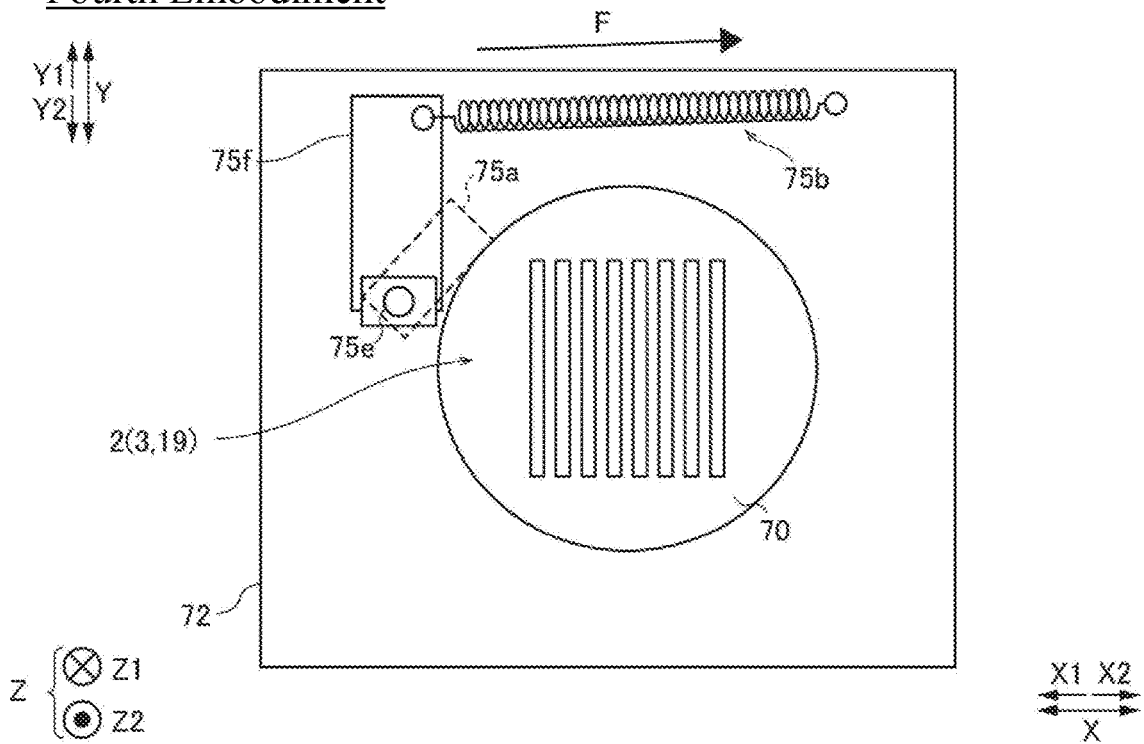
FIG. 16 is a schematic diagram of the grating rotation mechanism of the X-ray imaging apparatus according to the fourth embodiment as viewed from the Z2-direction.

As shown in FIG. 15, the grating rotation mechanism 7 according to the fourth embodiment includes a grating holder 70, a rotating section 71, a belt 74 connecting the grating holder 70 and the rotating section 71. The grating rotation mechanism 7 according to the fourth embodiment is a so-called belt-pulley mechanism. Further, in the fourth embodiment, as shown in FIG. 15, the grating rotation mechanism 7 further includes a stopper mechanism 75 (e.g., a stopper) switchable between a first state in which the grating is rotatable and a second state in which the grating is not rotatable (e.g., prevented from being rotated). The grating holder 70, the rotating section 71, the belt 74, and the stopper mechanism 75 are provided in the housing 72, respectively.

The stopper mechanism 75 includes a contact member 75a which comes into contact with the grating holder 70, an urging member 75b (see FIG. 16) for urging the contact member 75a against the grating holder 70, and a contact state release portion 75c for separating the contact member 75a from the grating holder 70 against the urging force. The contact member 75a includes, for example, a brake pad such as a rubber pad. The contact member 75a and the contact state release portion 75c are connected via the first intermediate member 75d. The contact member 75a is configured so as to bring the grating holder 70 into a non-rotatable state by abutting against the grating holder 70. The contact member 75a is configured to be rotatable about the central axis 75e and integrally with the first intermediate member 75d about the axis in the Z-direction.

The urging member 75b urges the contact member 75a in the X2-direction. Specifically, on the Z2 side of the grating rotation mechanism 7, one end side of the urging member 75b is connected to a second intermediate member 75f. The other end side of the urging member 75b is fixed to the housing 72. The second intermediate member 75f is connected to the contact member 75a via the central axis 75e. The urging member 75b urges the tensile force F in the X2-direction to the second intermediate member 75f to bring the contact member 75a into contact with the grating holder 70. The urging member 75b includes, for example, a coil spring. Further, the contact state release portion 75c is configured to apply a force in the Y2-direction to the first intermediate member 75d when power is supplied by the controller 6 (see FIG. 1). The contact state release portion 75c includes, for example, a solenoid. The force applied by the contact state release portion 75c to the contact member 75a via the first intermediate member 75d is set to be larger than the tensile force F applied to the contact member 75a by the urging member 75b.

(Switching of Rotation State of Grating by Stopper Mechanism)

In the fourth embodiment, the stopper mechanism 75 is configured to switch between a first state in which the grating is rotatable and a second state in which the grating is prevented from being rotated under the control of the controller 6. Specifically, under the control of the controller 6, the stopper mechanism 75 is configured to switch between a state in which the contact member 75*a* is in contact with the grating holder 70 and a state in which the contact member 75*a* is separated from the grating holder 70 by the contact state release portion 75*c*.

The urging member 75*b* always urges the tensile force F to the contact member 75*a* in the X2-direction. In the state in which no power is supplied by the controller 6, the contact state release portion 75*c* does not apply a force to the first intermediate member 75*d* in the Y2-direction. Therefore, when the contact state release portion 75*c* is not energized, only the tensile force F from the urging member 75*b* is applied to the contact member 75*a*. This state is a state in which the grating is not rotatable. In a state in which the grating cannot be rotated, the contact member 75*a* is urged in the X2-direction by the urging member 75*b*, so that the contact member 75*a* is in contact with the grating holder 70. Therefore, the grating holder 70 cannot be rotated.

On the other hand, when the contact state release portion 75*c* is energized by the controller 6, the contact state release portion 75*c* applies a force in the Y2-direction to the first intermediate member 75*d*, so that the contact member 75*a* is separated from the grating holder 70. This state is a state in which the grating is rotatable. When it is required to change the orientation of the grating with respect to the subject T, the controller 6 energizes the contact state release portion 75*c* so as to separate the contact member 75*a* to make the grating holder 70 rotatable. As described above, the stopper mechanism 75 is configured to switch between first and second states so that the grating is rotatable and is prevented from being rotated.

As shown in FIG. 15, in the fourth embodiment, the grating rotation mechanism 7 has an origin position detector 76 for detecting the origin position of the grating. The origin position detector 76 is configured to detect the position of the detection target portion 77 provided on the grating holder 70. The origin position detector 76 includes, for example, a photosensor. In the example shown in FIG. 15, the origin position detector 76 is provided on the line 82 extending in the Y2-direction from the center of the grating holder 70. In the fourth embodiment, the controller 6 is configured to store the position at which the detection target portion 77 is detected by the origin position detector 76 as the origin position of the grating in a storage unit (not shown).

The other configurations of the fourth embodiment are the same as those of the first to third embodiments.
(Effects of Fourth Embodiment)

In the fourth embodiment, the following effects can be obtained.

In the fourth embodiment, as described above, the grating rotation mechanism 7 further includes the stopper mechanism 75 switchable between states in which the grating is rotatable in which the grating is prevented from being rotated. With this, an unintentional grating rotation, such as a rotation due to an erroneous operation of the rotating section 71, can be suppressed by keeping the grating in the non-rotatable state at the time of imaging the subject T. As a result, it is possible to suppress an unintended misalignment in the rotation direction about the optical axis of the grating until imaging is performed after changing the orientation of the grating by the grating rotation mechanism 7.

Further, in the fourth embodiment, as described above, the stopper mechanism 75 includes the contact member 75*a* which comes into contact with the grating holder 70, the urging member 75*b* for urging the contact member 75*a* against the grating holder 70, and the contact state release portion 75*c* for separating the contact member 75*a* from the grating holder 70 against the urging force. Thus, by activating the contact state release portion 75*c*, it is possible to switch the grating by the urging force of the urging member 75*b* from the non-rotatable state to the rotatable state. As a result, it becomes possible to make the grating rotatable only when changing the orientation of the grating, so that it is possible to minimize the rotational position displacement of the grating with a simple configuration.

Further, in the fourth embodiment, as described above, the grating rotation mechanism 7 is further equipped with the origin position detector 76 for detecting the origin position of the grating. With this, when each grating is rotated, it can be easily confirmed whether each grating is arranged at the origin position. As a result, when each grating is rotated, each grating can easily be arranged at the initial position.

The other effects of the fourth embodiment are the same as those of the first embodiment.

Fifth Embodiment

Next, with reference to FIG. 17 and FIG. 18, an X-ray imaging apparatus 500 according to a fifth embodiment will be described. Unlike the first example in which a two-dimensional dark field image 13 of the subject T is generated, in the fifth embodiment, the X-ray imaging apparatus 500 is further provided with a rotation mechanism 18 for relative rotating the imaging system 17 constituted by the X-ray source 1, the detector 4, and the plurality of gratings and the subject T. The image processor 5 is configured to generate a three-dimensional dark field image from a plurality of dark field images 13 captured at a plurality of rotation angles while relatively rotating the subject T and the imaging system 17. The same reference numerals are allotted to the same configurations as those of the first embodiment, and the description thereof will be omitted.
(Configuration of X-Ray Imaging Apparatus)

First, with reference to FIG. 17, the configuration of the X-ray imaging apparatus 500 according to the fifth embodiment will be described.

Figure 17:
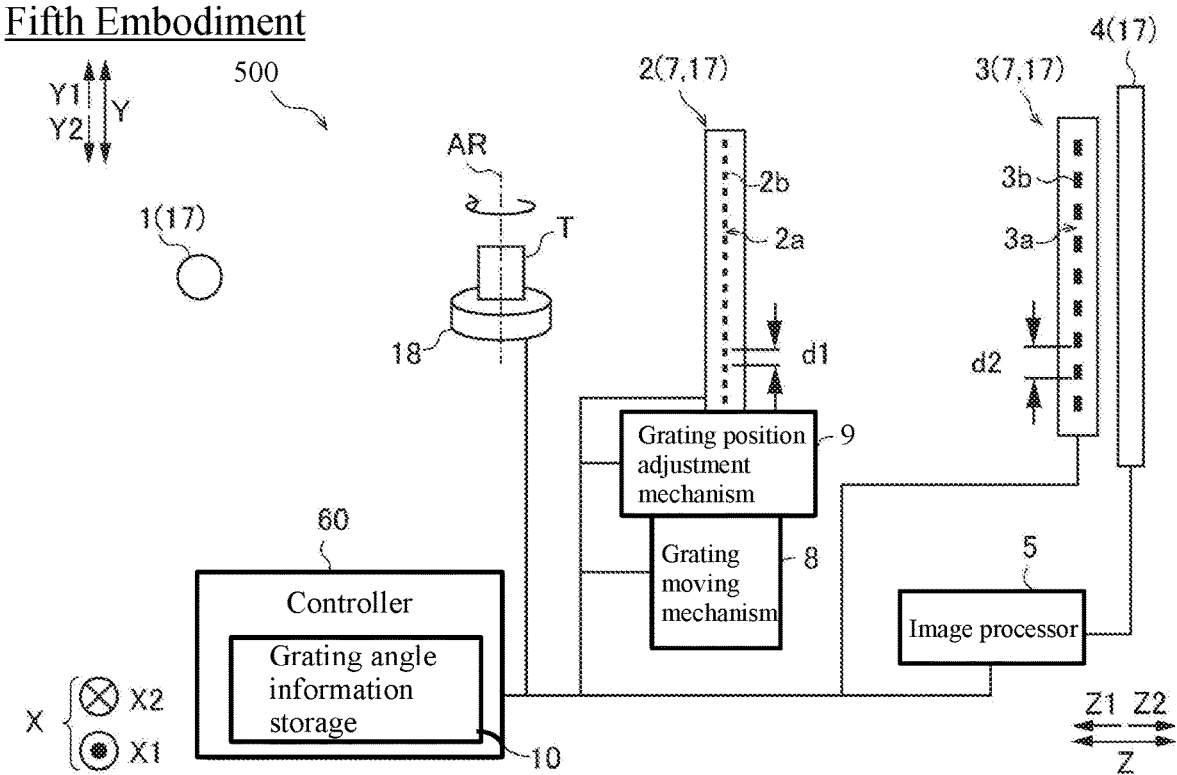
FIG. 17 is a schematic diagram of an X-ray imaging apparatus according to a fifth embodiment as viewed from the X-direction.
Figure 18:
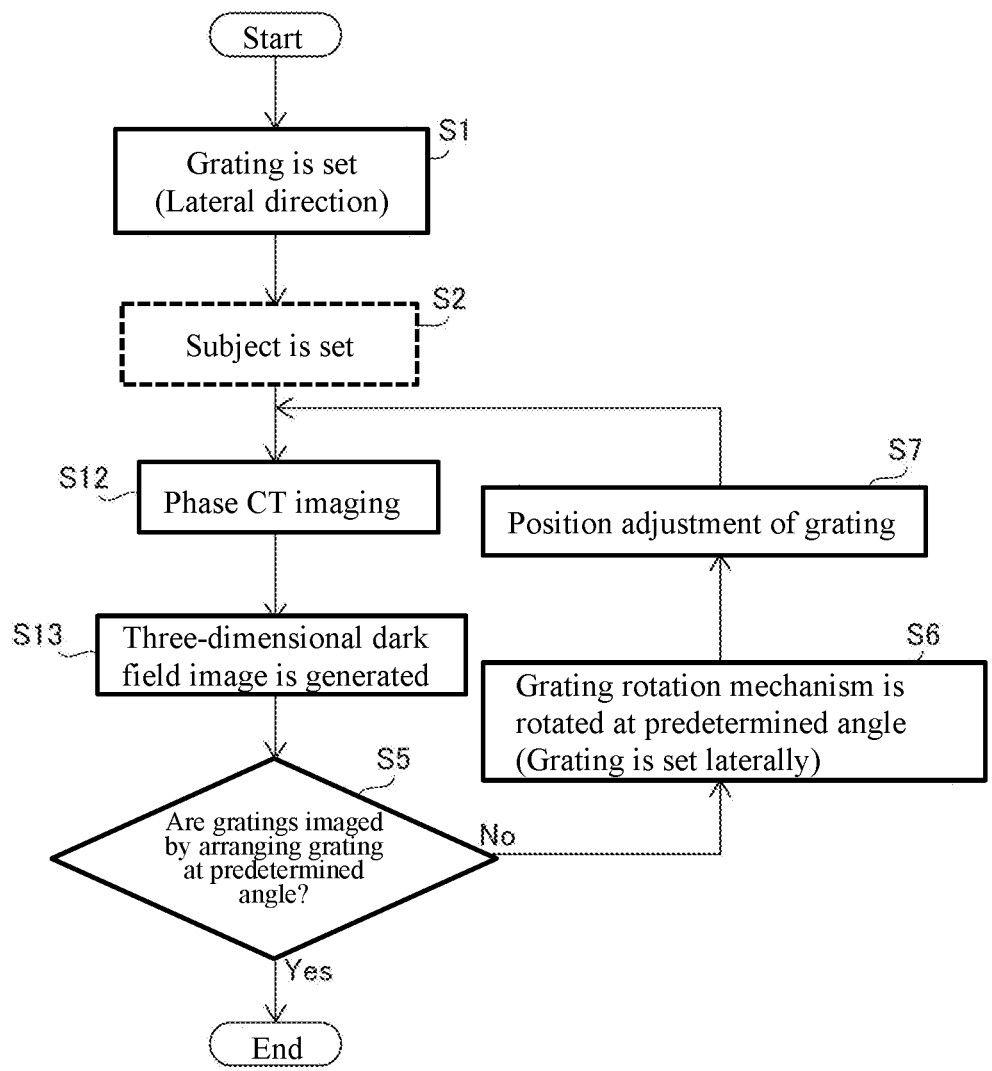
FIG. 18 is a flowchart of an imaging method by an X-ray imaging apparatus according to the fifth embodiment.

As shown in FIG. 17, the X-ray imaging apparatus 500 in the fifth embodiment further includes a rotation mechanism 18 for relative rotating the imaging system 17 constituted by the X-ray source 1, the detector 4, and the plurality of gratings and the subject T. Specifically, the rotation mechanism 18 is configured to relatively rotate the subject T and the imaging system 17 by rotating the subject T about the rotation axis AR. The rotation mechanism 18 is, for example, a rotatable subject stage configured to arrange a subject T thereon in a rotatable manner and including a motor and the like.
(Method of Imaging Subject)

Next, with reference to FIG. 18, the flow of the method of imaging the subject T by the X-ray imaging apparatus 500 according to the fifth embodiment will be described. The description of Steps similar to those of the first embodiment will be omitted.

In the fifth embodiment, the image processor 5 is configured to generate a three-dimensional dark field image from a plurality of dark field images 13 captured at a plurality of rotation angles while relatively rotating the subject T and the imaging system 17.

Specifically, in Step S1 and Step S2, the first grating 2 and the second grating 3 are arranged in a lateral direction (X-direction), and the subject T is arranged on the rotation mechanism 18. Thereafter, the process proceeds to Step S12.

In Step S12, the controller 6 images a plurality of dark field images 13 by translating the first grating 2 at a plurality of rotation angles while relatively rotating the subject T and the imaging system 17 by rotating the subject T via the rotation mechanism 18. Thereafter, the process proceeds to Step S13. In this specification, the technique of imaging by translating the first grating 2 while rotating the subject T is referred to as phase CT imaging.

In Step S13, the image processor 5 generates a three-dimensional dark field image from a plurality of dark field images 13 captured at a plurality of rotation angles while relatively rotating the subject T and the imaging system 17.

Thereafter, in Step S5, it is determined whether or not the imaging is performed while changing the direction of the grating. When imaging is performed by changing the orientation of the grating, the process is terminated. When imaging is not performed by changing the orientation of the grating, the process proceeds to Step S6.

The other configurations of the fifth embodiment are the same as those of the first to fourth embodiments.

(Effects of Fifth Embodiment)

In the fifth embodiment, the following effects can be obtained.

In the fifth embodiment, as described above, the rotation mechanism 18 for relative rotating the imaging system 17 constituted by the X-ray source 1, the detector 4, and the plurality of gratings and the subject T is further provided. The image processor 5 is configured to generate a three-dimensional dark field image from a plurality of dark field images 13 captured at a plurality of rotation angles while relatively rotating the subject T and the imaging system 17.

The scattering direction of the X-rays emphasized also by the direction of the rotation axis AR and the orientation of the grating when performing the relative rotation between the subject T and the imaging system 17 differs, and therefore there are cases that it is required to change the direction of the rotation axis AR when performing the relative rotation between the subject T and the imaging system 17. In addition, there are cases where it is required to change the orientation of the subject T with respect to the rotation axis AR when performing the relative rotation between the subject T and the imaging system 17. By performing the phase CT imaging as described above, without changing the direction of the rotation axis AR when performing the relative rotation between the subject T and the imaging system 17, it is possible to generate a three-dimensional dark field image captured by changing the orientation of the subject T with respect to the grating. Further, it is possible to generate a three-dimensional dark field image captured by changing the orientation of the subject T with respect to the gratings without changing the orientation of the subject T. As a result, it becomes unnecessary to combine the mechanism for changing the direction of the rotation axis AR and the mechanism for changing the orientation of the subject T when performing the relative rotation between the subject T and the imaging system 17, which can suppress complication of the device configuration.

The other effects of the fifth embodiment are the same as those of the first to fourth embodiments.

(Modifications)

It should be understood that the embodiments disclosed here are examples in all respects and are not restrictive. The scope of the present invention is shown by claims rather than the descriptions of the embodiments described above, and includes all changes (modifications) within the meaning of equivalent and the scope of claims.

For example, in the first to fifth embodiments, examples are described in which the grating moving mechanism 8 translates the first grating 2, but the present invention is not limited thereto. The grating to be translated may be any grating.

Further, in the first to fifth embodiments, examples are shown in which the grating position adjustment mechanism 9 adjusts the positional displacement of the first grating 2, but the present invention is not limited to this. The grating for adjusting the positional displacement may be any grating.

Further, in the aforementioned first to fifth embodiments, examples are shown in which the grating position adjustment mechanism 9 is disposed above the grating moving mechanism 8, but the present invention is not limited thereto. The grating moving mechanism 8 and the grating position adjustment mechanism 9 may be arranged below the separate gratings.

Figure 19:
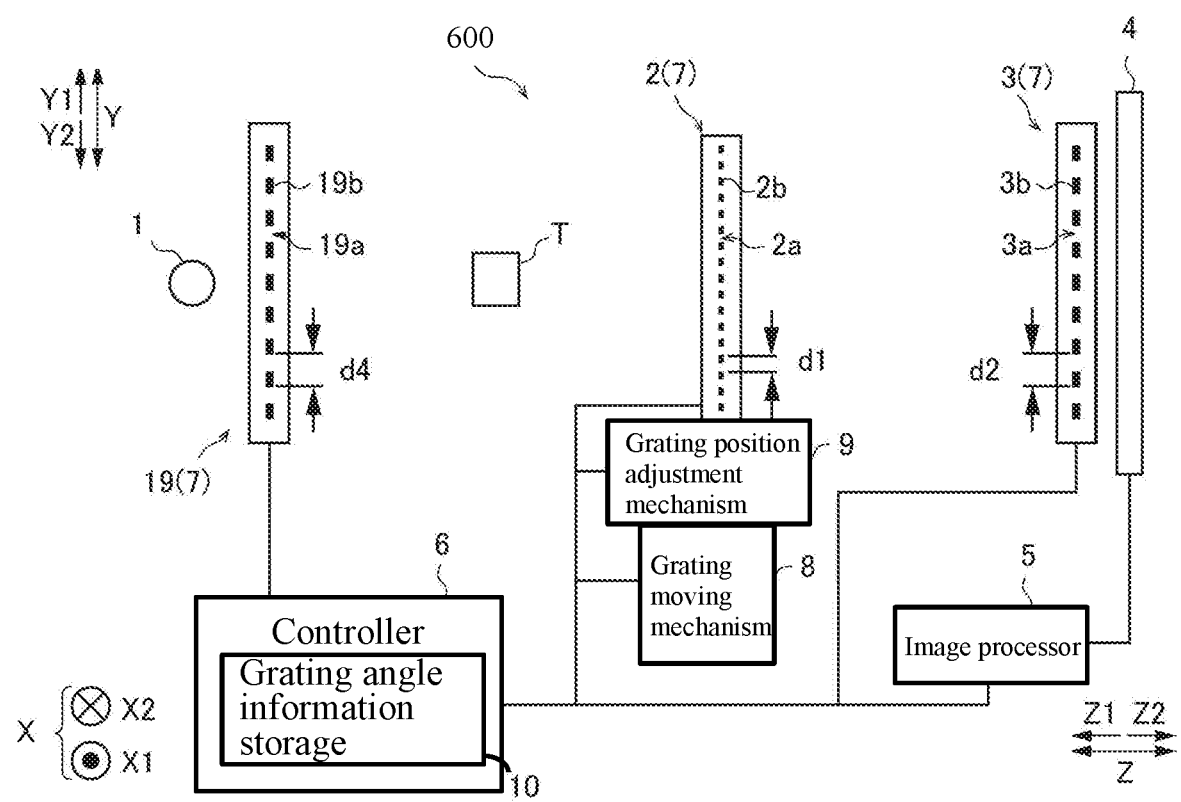
FIG. 19 is a schematic diagram of an X-ray imaging apparatus according to a first modification of the first embodiment as viewed from the X-direction.

Further, in the aforementioned first to fifth embodiments, although examples are shown in which only two gratings (i.e., the first grating 2 and the second grating 3) are provided as a plurality of gratings, the present invention is not limited to this. For example, like the X-ray imaging apparatus 600 shown in FIG. 19, a third grating 19 may be provided between the X-ray source 1 and the first grating 2 in the first to fifth embodiments described herein. The third grating 19 may have a plurality of slits 19a and X-ray absorption portions 19b arranged at predetermined periods (pitches) d4 in the Y-direction. The slits 19a and the X-ray absorption portions 19b are each formed so as to extend linearly. Further, the slits 19a and the X-ray absorption portions 19b are each formed so as to extend in parallel to each other. Further, the third grating 19 may be arranged between the X-ray source 1 and the first grating 2 and is irradiated by the X-rays from the X-ray source 1. The third grating 19 is configured to use the X-rays that have passed through each slit 19a as a line light source corresponding to the position of such slit 19a. Further, in the configuration in which the third grating 19 is provided, a grating rotation mechanism 7 for rotatably holding the third grating 19 is provided, and the third grating 19 is configured to be arranged at approximately the same rotation angle θ as the first grating 2 and the second grating 3 via the grating rotation mechanism 7 by a signal from the controller 6.

With this, the third grating 19 can enhance the coherence of the X-rays emitted from the X-ray source 1. As a result, it is possible to form the self-image 12 of the first grating 2 without depending on the focal spot size of the X-ray source 1, so that the freedom of selection of the X-ray source 1 can be improved.

Further, in the case in which the third grating 19 is additionally provided, in the plurality of gratings, the relative position of any one grating among the plurality of gratings is adjusted and the second grating 3 and the third grating 19 are configured to be arranged at relative and symmetrical relative positions based on the first grating 2. In other words, when each grating is arranged so that the distance between the third grating 19 and the first grating 2 is equal to the distance between the first grating 2 and the second grating 3, when the third grating 19 is arranged so as to be rotated by an angle θ with respect to the horizontal direction (X-direction) orthogonal to the optical axis direction (Z-direction) of the X-rays in the XY plane, and when the third grating 19 is arranged so as to be rotated by an angle θ in the opposite direction (minus direction) with respect to the horizontal direction (X-direction) orthogonal to the optical axis direction (Z-direction) of the X-rays in the XY plane, the moiré fringe 11 on the detector 4 disappears. Therefore, it can be regarded as an arrangement in which the position adjustment has been completed.

With this configuration, by arranging the position of any one of the first grating 2, the second grating 3, and the third grating 19 at relative and symmetrical relative positions based on the first grating 2, it is possible to perform the position adjustment of the plurality of gratings, and therefore the relative position of the plurality of gratings among the gratings can be easily adjusted.

In the first, second, fourth and fifth embodiments, examples are shown in which the grating is directed at approximately 90 degrees and approximately 0 degrees as an example of the vertical direction (Y-direction) and the lateral direction (X-direction), but the present invention is not limited to this. In the case of two directions substantially orthogonal to each other, the grating may be arranged in a direction other than approximately 90 degrees and approximately 0 degree. For example, each grating may be arranged at an orientation of 30 degrees and 120 degrees. In addition, as long as the gratings are arranged in different directions, they may be arranged at an arbitrary angle, and images may be captured by arranging the gratings at more angles than two directions like the third embodiment. However, when angles are close to each other, there is a possibility that a direction in which scattering of X-rays is not emphasized may be included, so it is preferable to image by arranging the grating in at least directions including two directions approximately orthogonal to each other.

Further, in the fifth embodiment, an example is shown in which the subject T is rotated, but the present invention is not limited to this. It may be configured to rotate the imaging system 17.

In the first to fifth examples, an example is shown in which the dark field image 13 is generated by translating the first grating 2, but the present invention is not limited thereto. For example, it may be configured to generate a dark field image 13 by a moiré single shot technique in which one of the plurality of gratings is rotated within the XY plane to form a moiré fringe 11 to capture an image.

In the first to fifth embodiments, examples are shown in which a phase grating is used as the first grating 2, but the present invention is not limited thereto. For example, an absorption grating may be used as the first grating 2.

Further, in the first, second, fourth, and fifth embodiments, examples are shown in which a carbon fiber reinforced plastic (CFRP) is imaged as the subject T, but the present invention is not limited thereto. For example, a glass fiber reinforced plastic (GFRP) or the like may be used as the subject. Any subject may be used as long as an internal structure having a directivity is included in the subject to be imaged.

In the first to fifth embodiments, examples are shown in which the subject T is arranged between the X-ray source 1 and the first grating 2, but the present invention is not limited thereto. The subject T may be arranged between the first grating 2 and the second grating 3. In any case, when the subject T is arranged at a position away from the first grating 2, since the phase sensitivity deteriorates, it is preferable to arrange the subject T at a position close to the first grating 2.

Further, in the fourth embodiment, an example is shown in which the rotating section 71 is provided for each of the grating rotation mechanisms 7, but the present invention is not limited thereto. For example, a plurality of grating rotation mechanisms 7 for rotating each grating may be configured to be rotated by a single rotating section 71.

Further, in the third embodiment, an example is shown in which the image processor 5 generates both the scattering oriented image 22 and the directivity intensity image 23, but the present invention is not limited thereto. For example, the image processor 5 may be configured to generate either the scattering oriented image 22 or the directivity intensity image 23. Further, the image processor 5 may be configured to generate a synthesized image synthesized by combining the total scattering image 20, the scattering oriented image 22, and the directivity intensity image 23 generated in the second embodiment.

Further, in the fourth embodiment, an example is shown in which the grating rotation mechanism 7, which is a belt-pulley mechanism, includes the stopper mechanism 75, but the present invention is not limited thereto. For example, as shown in the first embodiment, the grating rotation mechanism 7 may be configured to include a stopper mechanism 75 in a configuration including a gear-like grating holder 70 and a gear-like rotating section 71.

In the third embodiment, an example is shown in which the image processor 5 acquires the scattering oriented image 22 and the directivity intensity image 23 by the aforementioned equations (6) and (7), but the present invention is limited to this. For example, the image processor 5 may be configured to acquire a scattering oriented image 22 and a directivity intensity image 23 by fitting $I^{dark}k$ as a function of k by a sine curve (sine wave). Specifically, it is assumed that the dark field image 13 is a sinusoidal wave as shown in the following expression (8).

$$I^{dark}_k A + B \cos(\theta + \varphi) \qquad (8)$$

Here, $\theta$ is an angle of the grating. Further, $\varphi$ is phase information when $I^{dark}k$ is a function of k. The image processor 5 may be configured to obtain the scattering oriented image 22 and the directivity intensity image 23 by calculating $\varphi^{dark}(x, y)$ from the phase information $\varphi$ in the aforementioned equation (8) and calculating $V^{dark}(x, y)$ from B/A. Note that k (grating direction) is not limited to four directions. The direction in which the grating is arranged may be two directions. However, when the grating is arranged in two directions, depending on the direction of scattering of the X-rays by the subject T, it may be difficult to detect with high sensitivity, so the grating is preferably arranged in three or more directions. Also, it is not necessary for k to be equally spaced, but in that case, it is preferable to calculate the scattering oriented image 22 and the directivity intensity image 23 by a sine curve fitting method like the aforementioned formula (8).

The invention claimed is:

1. An X-ray imaging apparatus comprising:
    an X-ray source;
    a plurality of gratings including a first grating for forming a self-image by X-rays irradiated from the X-ray source and a second grating for causing interference with the self-image of the first grating;
    a detector configured to detect the X-rays irradiated from the X-ray source;
    a grating rotation mechanism configured to rotate each of the plurality of gratings in a plane orthogonal to an optical axis direction of the X-rays; and
    an image processor configured to generate at least a dark field image from an intensity distribution of the X-rays detected by the detector,
    wherein the image processor is configured to generate the dark field image captured by arranging the gratings at a plurality of angles in the plane orthogonal to the optical axis direction, and wherein the image processor is configured to generate a total scattering image representing the intensity of scattering of the X-rays by the subject by synthesizing a plurality of dark field images captured by arranging the gratings at the plurality of angles in the plane orthogonal to the optical axis direction.

2. The X-ray imaging apparatus as recited in claim 1, wherein the grating rotation mechanism is configured to arrange the plurality of gratings in at least any two directions among a vertical direction, a lateral direction, and an oblique direction in the plane orthogonal to the optical axis direction.

3. The X-ray imaging apparatus as recited in claim 1, further comprising:
a grating moving mechanism configured to move at least one of the plurality of gratings,
wherein the grating moving mechanism is configured to move the at least one of the plurality of gratings together with the grating rotation mechanism after rotating the plurality of gratings.

4. The X-ray imaging apparatus as recited in claim 3, wherein the grating moving mechanism is configured to move the grating in a vertical direction or a lateral direction in the plane orthogonal to the optical axis direction, change a direction in which the grating is moved according to an arrangement direction of the plurality of gratings, and move the at least one of the plurality of gratings in a direction in which a distance of a translational movement becomes small when translating any one of the plurality of gratings by at least one grating period or more.

5. The X-ray imaging apparatus as recited in claim 3, further comprising:
a grating position adjustment mechanism configured to adjust a relative position of at least one of a plurality of gratings among the plurality of gratings,
wherein the grating rotation mechanism is configured to be held on the grating moving mechanism via the grating position adjustment mechanism.

6. The X-ray imaging apparatus as recited in claim 5, further comprising:
a controller configured to calculate an adjustment amount of the grating by the grating position adjustment mechanism based on a moiré fringe that occurs after rotating the plurality of gratings by the grating rotation mechanism.

7. The X-ray imaging apparatus as recited in claim 1, wherein the grating rotation mechanism includes a grating holder configured to hold the grating and a rotating section configured to rotate the grating holder.

8. The X-ray imaging apparatus as recited in claim 7, wherein the grating rotation mechanism further includes a stopper mechanism configured to switch between a first state in which the grating is rotatable and a second state in which the grating is prevented from being rotated.

9. The X-ray imaging apparatus as recited in claim 8, wherein the stopper mechanism includes a contact member that comes into contact with the grating holder, an urging member configured to urge the contact member against the grating holder and a contact state release portion configured to separate the contact member from the grating holder against an urging force of the urging member.

10. The X-ray imaging apparatus as recited in claim 7, wherein the grating rotation mechanism further includes an origin position detector configured to detect an origin position of the grating.

11. The X-ray imaging apparatus as recited in claim 1, further comprising:
storage configured to store angle information of the plurality of gratings rotated by the grating rotation mechanism.

12. The X-ray imaging apparatus as recited in claim 1, wherein the image processor is configured to further generate at least either one of a scattering oriented image representing directivity of scattering of the X-rays by the subject and a directivity intensity image representing strength of directivity of scattering of the X-rays by the subject using the plurality of dark field images different in the angle of the plurality of gratings.

13. The X-ray imaging apparatus as recited in claim 12, wherein the image processor is configured to generate a scattering oriented image in which the directivity of scattering of the X-rays and a color are displayed in an associated manner.

14. The X-ray imaging apparatus as recited in claim 1, wherein the image processor is configured to acquire a feature amount of the subject from the image generated by synthesizing the plurality of dark field images.

15. The X-ray imaging apparatus as recited in claim 14, wherein
the image processor is configured to acquire information on an internal structure having a directivity within the subject as the feature amount of the subject, and
the information on the internal structure having a directivity within the subject includes at least a length of the internal structure having a directivity and a width of the internal structure having a directivity.

16. The X-ray imaging apparatus as recited in claim 1, wherein the plurality of gratings further includes a third grating arranged between the X-ray source and the first grating.

17. The X-ray imaging apparatus as recited in claim 16, wherein it is configured such that, in the plurality of gratings, a relative position of any one of the plurality of gratings among the gratings is adjusted, so that the second grating and the third grating are arranged at relative and symmetrical relative positions based on the first grating.

18. An X-ray imaging apparatus comprising:
an X-ray source;
a plurality of gratings including a first grating for forming a self-image by X-rays irradiated from the X-ray source and a second grating for causing interference with the self-image of the first grating;
a detector configured to detect the X-rays irradiated from the X-ray source;
a grating rotation mechanism configured to rotate each of the plurality of gratings in a plane orthogonal to an optical axis direction of the X-rays;
an image processor configured to generate at least a dark field image from an intensity distribution of the X-rays detected by the detector; and
a rotation mechanism configured to relatively rotate an imaging system and a subject, the imaging system including the X-ray source, the detector, and the plurality of gratings,
wherein the image processor is configured to generate the dark field image captured by arranging the gratings at a plurality of angles in the plane orthogonal to the optical axis direction, and
wherein the image processor is configured to generate a three-dimensional dark field image from a plurality of dark field images captured at a plurality of rotation angles while relatively rotating the subject and the imaging system.

* * * * *